US010793605B2

(12) United States Patent
Ly et al.

(10) Patent No.: US 10,793,605 B2
(45) Date of Patent: *Oct. 6, 2020

(54) CONFORMATIONALLY-PREORGANIZED, MINIPEG-CONTAINING γ-PEPTIDE NUCLEIC ACIDS

(71) Applicant: CARNEGIE MELLON UNIVERSITY, Pittsburgh, PA (US)

(72) Inventors: Danith H. Ly, Pittsburgh, PA (US); Srinivas Rapireddy, Pittsburgh, PA (US); Bichismita Sahu, Pittsburgh, PA (US)

(73) Assignee: CARNEGIE MELLON UNIVERSITY, Pittsburgh, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/362,579

(22) Filed: Mar. 22, 2019

(65) Prior Publication Data
US 2019/0292227 A1    Sep. 26, 2019

Related U.S. Application Data

(60) Continuation of application No. 16/145,075, filed on Sep. 27, 2018, now Pat. No. 10,364,272, which is a
(Continued)

(51) Int. Cl.
*C07H 15/00* (2006.01)
*C07K 14/00* (2006.01)
(Continued)

(52) U.S. Cl.
CPC ............ *C07K 14/003* (2013.01); *A61K 47/60* (2017.08); *C07C 229/12* (2013.01);
(Continued)

(58) Field of Classification Search
CPC ................................................... C07K 14/003
(Continued)

(56) References Cited

U.S. PATENT DOCUMENTS 5,977,296 A   11/1999  Nielsen et al.
6,063,569 A    5/2000  Gildea et al.
(Continued)

FOREIGN PATENT DOCUMENTS

WO    WO-02/097134 A2    12/2002
WO    WO-2004/024757 A2   3/2004

OTHER PUBLICATIONS

Dragulescu-Andrasi Anca et al., "A simple gamma-backbone modification preorganizes peptide nucleic acid into a helical structure", Journal of the American Chemical Society, Aug. 2006, vol. 128, No. 31, pp. 10258-10267 (Published on-line Jul. 2006).
(Continued)

*Primary Examiner* — Jezia Riley
(74) *Attorney, Agent, or Firm* — Foley & Lardner LLP

(57) ABSTRACT

The present invention relates to γ-PNA monomers according to Formula I where substituent groups $R_1$, $R_2$, $R_3$, $R_4$, $R_5$, $R_6$, B and P are defined as set forth in the specification. The invention also provides methodology for synthesizing compounds according to Formula I and methodology for synthesizing PNA oligomers that incorporate one or more Formula I monomers.

19 Claims, 10 Drawing Sheets

Specification includes a Sequence Listing.

Related U.S. Application Data division of application No. 14/921,755, filed on Oct. 23, 2015, now Pat. No. 10,093,700, which is a continuation of application No. 14/110,689, filed as application No. PCT/US2012/032459 on Apr. 6, 2012, now Pat. No. 9,193,758.

(60) Provisional application No. 61/516,838, filed on Apr. 8, 2011, provisional application No. 61/516,812, filed on Apr. 8, 2011.

(51) Int. Cl.

| | |
|---|---|
| *A61K 47/60* | (2017.01) |
| *C07D 239/54* | (2006.01) |
| *C07D 473/18* | (2006.01) |
| *C07D 473/34* | (2006.01) |
| *C07D 239/47* | (2006.01) |
| *C07K 1/08* | (2006.01) |
| *C07C 229/12* | (2006.01) |
| *C07C 271/20* | (2006.01) |
| *C07K 1/04* | (2006.01) |
| *C08G 69/10* | (2006.01) |

(52) U.S. Cl.
CPC .......... *C07C 271/20* (2013.01); *C07D 239/47* (2013.01); *C07D 239/54* (2013.01); *C07D 473/18* (2013.01); *C07D 473/34* (2013.01); *C07K 1/04* (2013.01); *C07K 1/08* (2013.01); *C08G 69/10* (2013.01)

(58) Field of Classification Search
USPC ......................................................... 536/4.1
See application file for complete search history.

(56) References Cited

U.S. PATENT DOCUMENTS

| | | |
|---|---|---|
| 6,107,470 A | 8/2000 | Nielsen et al. |
| 6,121,418 A | 9/2000 | Breipohl et al. |
| 6,169,169 B1 | 1/2001 | Hyldig-Nielsen et al. |
| 6,632,922 B1 | 10/2003 | Deming et al. |
| 7,223,833 B1 | 5/2007 | Nielsen et al. |
| 9,193,758 B2 | 11/2015 | Ly et al. |
| 10,093,700 B2 | 10/2018 | Ly et al. |
| 10,160,787 B2 | 12/2018 | Ly et al. |
| 2005/0009041 A1 | 1/2005 | Buchardt et al. |
| 2006/0159619 A1 | 7/2006 | Becker et al. |
| 2019/0062378 A1 | 2/2019 | Ly et al. |

OTHER PUBLICATIONS

Dueholm et al., "Synthesis of Peptide Nucleic Acid Monomers Containing the Four Natural Nucleobases: Thymine, Cytosine, Adenine, and Guanine and Their Oligomerization," J. Org. Chem., No. 59, pp. 5767-5773, Sep. 1994.

European Search Report dated Nov. 14, 2014 issued in European Application No. 12767656.7.

Hyrup and Nielsen, "Peptide Nucleic Acids (PNA): Synthesis, Properties and Potential Applications", Bioorganic & Medicinal Chemistry, vol. 4, No. 1, pp. 5-23, Jan. 1996.

Hyrup et al., "A Flexible and Positively Charged PNA Analogue With an Ethylene-Linker to the Nucleobase: Synthesis and Hybridization Properties", Bioorganic and Medicinal Chemistry Letters, vol. 6, No. 10, pp. 1083-1088, May 1996.

PCT/US2012/032459 International Search Report dated Oct. 29, 2012.

Pensato et al, "gamma-Hydroxymethyl PNAs: Synthesis, interaction and DNA and inhibition of protein/DNA interactions", Bioorganic Chemistry, No. 38, pp. 196-201, Oct. 2010.

Puschl, "Peptide Nucleic Acids (PNAs) with a Functional Backbone", Tetrahedron Letters, No. 39, pp. 4707-4710, Jun. 1998.

Sahu et al., Synthesis and Characterization of Conformationally Preorganized, (R)-Diethylene Glycol-Containing y-Peptide Nucleic Acids with Superior Hybridization Properties and Water Solubility, J. Org. Chem., May 2011, No. 76, pp. 5614-5627.

Sahu et al., "Synthesis of Conformationally Preorganized and Cell-Permeable Guanidine-Based y-Peptide Nucleic Acids (yGPNAs)," The Journal of Organic Chemistry, vol. 74, No. 4 (Feb. 2009) pp. 1509-11516, XP55187182.

Yeh et al., "Crystal Structure of Chiral y-PNA with Complementary DNA Strand: Insights into the Stability and Specificity of Recognition and Conformational Preorganization", J. Am. Chem., Aug. 2010, No. 132, pp. 10717-10727 (published on-line Jul. 2010).

SEQUENCE LISTING

<160> NUMBER OF SEQ ID NOS: 12

<210> SEQ ID NO 1
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
gcatgtttga                                                                10

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(6)
<223> OTHER INFORMATION: R-MP-gamma-backbone modified nucleotide

<400> SEQUENCE: 2
gcatgtttga                                                                10

<210> SEQ ID NO 3
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: R-MP-gamma-backbone modified nucleotide
<220> FEATURE:
<221> NAME/KEY: modified_base
<222> LOCATION: (6)..(6)
<223> OTHER INFORMATION: R-MP-gamma-backbone modified nucleotide
<220> FEATURE:
<221> NAME/KEY: modified_base
<222> LOCATION: (8)..(8)
<223> OTHER INFORMATION: R-MP-gamma-backbone modified nucleotide

<400> SEQUENCE: 3
gcatgtttga                                                                10

<210> SEQ ID NO 4
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: R-MP-gamma-backbone modified nucleotide
<220> FEATURE:
<221> NAME/KEY: modified_base
<222> LOCATION: (4)..(4)
<223> OTHER INFORMATION: R-MP-gamma-backbone modified nucleotide
<220> FEATURE:
<221> NAME/KEY: modified_base
<222> LOCATION: (6)..(6)
<223> OTHER INFORMATION: R-MP-gamma-backbone modified nucleotide

```
<220> FEATURE:
<221> NAME/KEY: modified_base
<222> LOCATION: (8)..(8)
<223> OTHER INFORMATION: R-MP-gamma-backbone modified nucleotide
<220> FEATURE:
<221> NAME/KEY: modified_base
<222> LOCATION: (10)..(10)
<223> OTHER INFORMATION: R-MP-gamma-backbone modified nucleotide

<400> SEQUENCE: 4
gcatgtttga                                                          10

<210> SEQ ID NO 5
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(10)
<223> OTHER INFORMATION: R-MP-gamma-backbone modified nucleotide

<400> SEQUENCE: 5
gcatgtttga                                                          10

<210> SEQ ID NO 6
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
acgggtagaa taacat                                                   16

<210> SEQ ID NO 7
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(8)
<223> OTHER INFORMATION: R-MP-gamma-backbone modified nucleotide

<400> SEQUENCE: 7
acgggtagaa taacat                                                   16

<210> SEQ ID NO 8
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: R-MP-gamma-backbone modified nucleotide
<220> FEATURE:
<221> NAME/KEY: modified_base
<222> LOCATION: (8)..(8)
<223> OTHER INFORMATION: R-MP-gamma-backbone modified nucleotide
```

```
<220> FEATURE:
<221> NAME/KEY: modified_base
<222> LOCATION: (15)..(15)
<223> OTHER INFORMATION: R-MP-gamma-backbone modified nucleotide

<400> SEQUENCE: 8
acgggtagaa taacat                                                      16

<210> SEQ ID NO 9
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(3)
<223> OTHER INFORMATION: R-MP-gamma-backbone modified nucleotide
<220> FEATURE:
<221> NAME/KEY: modified_base
<222> LOCATION: (6)..(6)
<223> OTHER INFORMATION: R-MP-gamma-backbone modified nucleotide
<220> FEATURE:
<221> NAME/KEY: modified_base
<222> LOCATION: (9)..(9)
<223> OTHER INFORMATION: R-MP-gamma-backbone modified nucleotide
<220> FEATURE:
<221> NAME/KEY: modified_base
<222> LOCATION: (12)..(12)
<223> OTHER INFORMATION: R-MP-gamma-backbone modified nucleotide
<220> FEATURE:
<221> NAME/KEY: modified_base
<222> LOCATION: (15)..(15)
<223> OTHER INFORMATION: R-MP-gamma-backbone modified nucleotide

<400> SEQUENCE: 9
acgggtagaa taacat                                                      16

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: R-MP-gamma-backbone modified nucleotide
<220> FEATURE:
<221> NAME/KEY: modified_base
<222> LOCATION: (4)..(4)
<223> OTHER INFORMATION: R-MP-gamma-backbone modified nucleotide
<220> FEATURE:
<221> NAME/KEY: modified_base
<222> LOCATION: (6)..(6)
<223> OTHER INFORMATION: R-MP-gamma-backbone modified nucleotide
<220> FEATURE:
<221> NAME/KEY: modified_base
<222> LOCATION: (8)..(8)
<223> OTHER INFORMATION: R-MP-gamma-backbone modified nucleotide
<220> FEATURE:
<221> NAME/KEY: modified_base
<222> LOCATION: (10)..(10)
<223> OTHER INFORMATION: R-MP-gamma-backbone modified nucleotide
<220> FEATURE:
<221> NAME/KEY: modified_base
<222> LOCATION: (12)..(12)
<223> OTHER INFORMATION: R-MP-gamma-backbone modified nucleotide
<220> FEATURE:
<221> NAME/KEY: modified_base
<222> LOCATION: (14)..(14)
<223> OTHER INFORMATION: R-MP-gamma-backbone modified nucleotide
```

```
<220> FEATURE:
<221> NAME/KEY: modified_base
<222> LOCATION: (16)..(16)
<223> OTHER INFORMATION: R-MP-gamma-backbone modified nucleotide

<400> SEQUENCE: 10
acgggtagaa taacat                                                     16

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, t or g

<400> SEQUENCE: 11 tcanacatgc                                                            10

<210> SEQ ID NO 12
<211> LENGTH: 10
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (4)..(4)
<223> OTHER INFORMATION: a, c, u or g

<400> SEQUENCE: 12 ucanacaugc                                                            10
```

CONFORMATIONALLY-PREORGANIZED, MINIPEG-CONTAINING γ-PEPTIDE NUCLEIC ACIDS

CROSS-REFERENCE TO RELATED APPLICATIONS

This application is a continuation of U.S. patent application Ser. No. 16/145,075, filed Sep. 27, 2018, which is a divisional of U.S. patent application Ser. No. 14/921,755, filed Oct. 23, 2015 (now U.S. Pat. No. 10,093,700), which is a continuation of U.S. patent application Ser. No. 14/110,689, filed Jan. 17, 2014 (now U.S. Pat. No. 9,193,758), which is a U.S. national stage of PCT/US2012/032459, filed Apr. 6, 2012, which claims priority from U.S. provisional applications No. 61/516,812 and No. 61/516,838, both filed Apr. 8, 2011. The contents of these applications are incorporated herein by reference in their entirety.

GOVERNMENT LICENSE RIGHTS

This invention was made with government support under Grant No. GM76251, awarded by the National Institutes of Health, and Grant No. CHE-1012467, awarded by the National Service Foundation. The government has certain rights in this invention.

SEQUENCE LISTING

The instant application contains a Sequence Listing which has been submitted electronically in ASCII format and is hereby incorporated by reference in its entirety. Said ASCII copy, created on Dec. 11, 2015, is named 101700-0111_SL.txt and is 5,969 bytes in size.

BACKGROUND OF THE INVENTION

PNAs are a class of nucleic acid mimics in which the naturally occurring sugar phosphodiester backbone is replaced with N-(2-aminoethyl) glycine units. See Nielsen, P. E.; et. al., *Science* 1991, 254, 1497-1500. Because of the homomorphous nature of the backbone and linker, PNAs can hybridize to complementary DNA and RNA through normal Watson-Crick base-pairing just as the natural counterparts, but with higher affinity and sequence selectivity. See Egholm, M., et al., *Nature* 1993, 365, 566-568.

PNAs are also capable of invading selected sequences of double-stranded DNA (dsDNA) attributed in large part to the lack of electrostatic repulsion between the PNA and DNA strands. While the underlying mechanism for high sequence selectivity of a PNA hybrid with either a DNA or RNA is not fully understood, structural studies suggested that hydration may play a key role in binding and selectivity. For instance, X-ray structural data of PNA-DNA and PNA-RNA duplexes indicates that a molecule of water bridges the amide proton in the backbone to the adjacent nucleobase rigidifying the PNAs backbone and preventing sequence mismatches thereby making the sequence mismatch less accommodating.

In addition the ability of PNAs to hybridize to DNA or RNA with high sequence selectivity, biochemical studies indicate that PNAs posses enhanced nucleolytic and proteolytic stability, most likely due to their unnatural backbone that prevents or slows down the physiological degradation of PNA's by proteases or nucleases.

Despite the many appealing features that make PNAs attractive as molecular reagents for biology, biotechnology and medicine, PNAs have some drawbacks as compared to other classes of oligonucleotides. PNAs have a charge neutral backbone as a result of which PNAs have poor water solubility, the propensity to aggregate and adhere to surfaces and adhere to other macromolecules in a nonspecific manner. This inherent property of non-specific aggregation and surface adherence presents a technical challenge for the handling and processing of PNAs.

While considerable efforts have been made to address these problems, several of the prior art efforts have focused on incorporating charged amino acid residues at the termini or in the interior of a PNA oligomer, the inclusion of polar groups in the backbone, the replacement of the original aminoethylglycyl backbone skeleton with a negatively-charged scaffold, the conjugation of high molecular weight polyethylene glycol (PEG) to one of the oligomer termini, or fusion of a PNA to a DNA to generate a chimeric oligomer to improve water solubility. However, these chemical modifications are often achieved at the expense of binding affinity and/or sequence specificity.

Additionally, the high costs associated with synthesis of PNAs has limited their incorporation as reagents routinely used in diagnostic assays, gene therapy and other biochemical assays.

SUMMARY OF THE INVENTION

The present invention addresses drawbacks of the conventional technology by providing a hydrophilic PNA moiety with improved hybridization properties, water solubility and biocompatibility. More particularly, the invention relates to the design, synthesis, and uses of a hydrophilic (R)-miniPEG PNA unit having a polyethyleneglycol (miniPEG or "MP") sidechain at the γ-carbon of the PNAs' backbone.

According to one embodiment, therefore, the invention provides compound according to Formula I

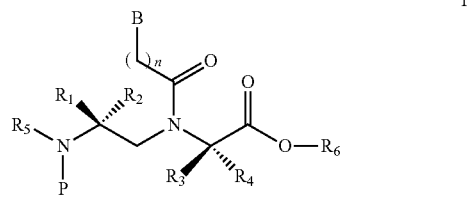

In Formula I, B is a nucleic acid base selected from adenine, guanine, cytosine, thymine or uracil. Substituent groups $R_1$, $R_2$ and $R_5$ each independently are selected from the group consisting of H, linear or branched $(C_1\text{-}C_8)$alkyl, $(C_2\text{-}C_8)$alkenyl, $(C_2\text{-}C_8)$alkynyl, $(C_1\text{-}C_8)$hydroxyalkyl, $(C_3\text{-}C_8)$aryl, $(C_3\text{-}C_8)$cycloalkyl, $(C_3\text{-}C_8)$aryl$(C_1\text{-}C_6)$alkylene, $(C_3\text{-}C_8)$cycloalkyl$(C_1\text{-}C_6)$alkylene, $-CH_2-(OCH_2-CH_2)_q\text{OP}_1$, $-CH_2-(OCH_2-CH_2)_q-\text{NHP}_1$, $-CH_2-(OCH_2-CH_2-O)_q-\text{SP}_1$ and $-CH_2-(SCH_2-CH_2)_q-\text{SP}_1$.

Substituents $R_3$ and $R_4$ each independently are H while $R_6$ is selected from the group consisting of H, linear or branched $(C_1\text{-}C_8)$alkyl, substituted or unsubstituted $(C_3\text{-}C_8)$ aryl and $(C_3\text{-}C_8)$aryl$(C_1\text{-}C_6)$alkylene.

According to Formula I, P is selected from the group consisting of H, 9-fluorenylmethyloxy carbonyl, Boc, benzyloxycarbonyl, tosylate, benzyl, alloc, trityl, dimethoxytrityl and monomethoxytrityl and substituent $P_1$ is selected from the group consisting of H, $(C_1\text{-}C_8)$alkyl, $(C_2\text{-}C_8)$ alkenyl, $(C_2\text{-}C_8)$alkynyl, $(C_3\text{-}C_8)$aryl, $(C_3\text{-}C_8)$cycloalkyl, $(C_3\text{-}C_8)$aryl$(C_1\text{-}C_6)$alkylene and $(C_3\text{-}C_8)$cycloalkyl$(C_1\text{-}C_6)$alkylene. Subscripts n and q are each independently integers between 0 and 10 inclusive.

According to one embodiment, each of $R_1$ and $R_2$ in a Formula I compound is independently —$CH_2$—O—($CH_2$—$CH_2$—O$)_q P_1$. For some Formula I compounds each of $R_1$ is $CH_2$—(O—$CH_2$—$CH_2$-$)_n OP_1$ and $R_2$ is selected from the group consisting of H, linear or branched $(C_1\text{-}C_8)$alkyl, $(C_2\text{-}C_8)$alkenyl, $(C_2\text{-}C_8)$alkynyl, $(C_1\text{-}C_8)$hydroxyalkyl, $(C_3\text{-}C_8)$aryl, $(C_3\text{-}C_8)$cycloalkyl, $(C_3\text{-}C_8)$aryl$(C_1\text{-}C_6)$alkylene, $(C_3\text{-}C_8)$cycloalkyl$(C_1\text{-}C_6)$alkylene, —$CH_2$—(OCH$_2$—$CH_2)_q$—NHP1, —$CH_2$—(OCH$_2$—$CH_2$—O$)_q$—$SP_1$ and —$CH_2$—(SCH$_2$—$CH_2)_q$—$SP_1$. For certain Formula I compounds $R_1$ is —$CH_2$—(O—$CH_2$—$CH_2$-$)_q OP_1$, $R_2$ is H and substituent $P_1$ is H or $(C_1\text{-}C_8)$alkyl.

Formula I compounds are chiral. The stereochemical purity of a Formula I compound is in the range from about 80% to about 99% at the Cγ-position. In one embodiment the stereochemical purity is at least 90% at the Cγ-position. According to yet another embodiment the stereochemical purity of a Formula I compound is at least 99% at the Cγ-position.

The present invention also provides a method for preparing a compound according to Formula I. According to the inventive method, a compound of Formula II

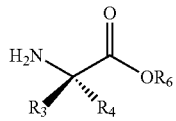

(II)

is contacted with a Formula III

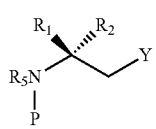

(III)

compound to obtain a compound according to Formula IV

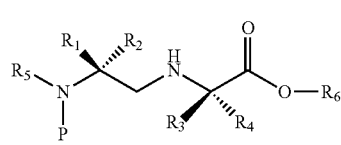

IV

The Formula IV compound is contacted with a compound according to Formula V

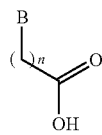

(V)

to give a Formula I compound. Substituent groups B, $R_1$, $R_2$, $R_3$, $R_4$, $R_5$, $R_6$, P and $P_1$ are defined above. Substituent Y in Formula III is selected from the group consisting of bromine, iodine, 4-toluenesulfonate and methanesulfonate.

According to the inventive synthetic methodology, the step of contacting a Formula IV compound with a Formula V compound is effected in the presence of a coupling agent selected from the group consisting of dicyclohexylcarbodiimide, carbonyldiimidazole, O-(benzotriazol-1-yl)-N,N,N'N'-tetramethyluronium hexafluorophosphate (HBTU), (benzotraizol-1-yloxy)tris(dimethylamino)phosphonium hexafluorophosphate (BOP) and O-(7-azabenzotriazol-1-yl)-N,N,N'N'-tetramethyluronium hexafluorophosphate (HATU). in a polar aprotic solvent.

In one embodiment, the present invention provides a method for synthesizing a compound of Formula III by contacting

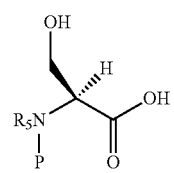

with a $CH_3$—(O—$CH_2$—$CH_2$-$)_q OX$ group to obtain

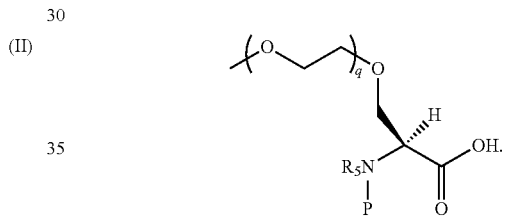

The carboxylic acid group of the polyethyleneoxy product is further reduced to the corresponding alcohol; and then brought in contact with a reagent to obtain the Formula III compound.

According to one embodiment the alcohol is brought in contact with a reagent selected from the group consisting of methanesulfonyl chloride, 4-toluenesulfonyl chloride and sodium iodide in an aprotic solvent. When the alcohol is contacted with sodium iodide the contacting step is effected in the presence of a catalyst, such as zirconium (IV) chloride.

In one embodiment the present invention provides a method for synthesizing a peptide nucleic acid (PNA) oligomer having a pre-determined sequence, by contacting a solid support with an allyl linker according to Formula VI

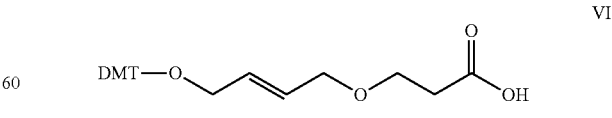

VI

De-protecting the DMT group to obtain the corresponding alcohol which is then brought in contact with a first PNA monomer or a γPNA monomer depending on the PNA oligomer sequence. The carboxylic acid group of the first monomer is activated prior to contact with the allyl linker-resin. Following coupling of the first PNA residue to the resin deprotecting the amino group of the first PNA residue.

Activating the carboxylic acid group of a second sequence specific PNA monomer or γPNA monomer and contacting this activated carboxylic acid PNA with the amino group of the PNA residue attached to the resin. The steps described above are repeated to synthesize the peptide nucleic acid (PNA) oligomer comprising at least one γPNA monomer.

DETAILED DESCRIPTION OF THE PREFERRED EMBODIMENTS

Figure 1A:
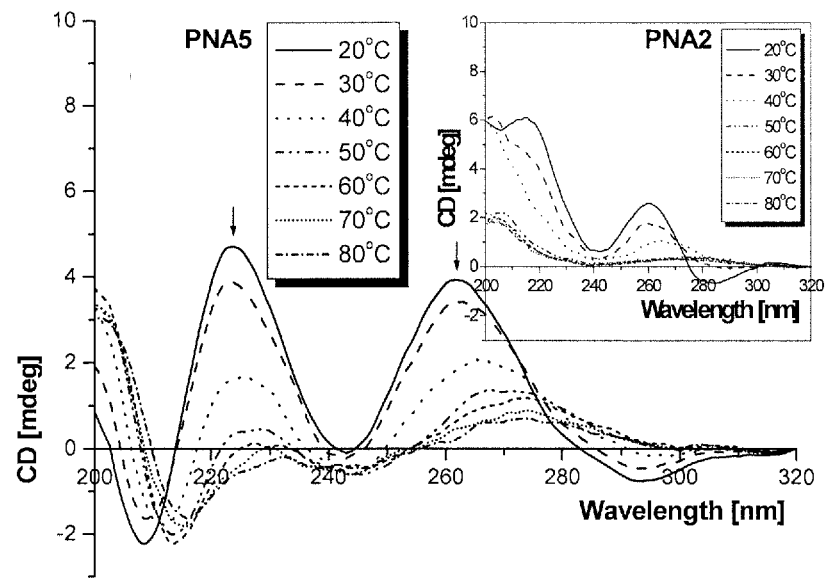
FIG. 1A illustrates CD spectra of PNA5 and PNA2 (Inset) as a function of temperature. Melting transition ($T_m$) of PNA2 through 5 as determined by CD, monitored at 260 nm. The oligomer concentration was 5 µM, prepared in 10 mM sodium phosphate buffer at pH 7.4.

The present invention concerns a new class of conformationally-preorganized, MiniPEG-containing γPNA monomers that possess good water solubility, exhibit superior hybridization properties, biocompatibility, can readily invade double-stranded DNA and secondary structures of RNA, and are capable of undergoing facile chemical diversification, such as by the introduction of functionally diverse chemical groups at one or both termini of the PNA monomer or within the PNAs backbone. Thus, the invention provides compounds according to Formula I, as well as methodology for synthesizing a Formula I γPNA monomer and also for synthesizing a PNA monomer having one or more Formula I γPNA monomers.

Definitions

Within the context of the present invention, the term "miniPEG" or "MP" are used interchangeably and refer to a single poly-ethyleneglycol (PEG) unit or a polymer of PEG comprising from 2-50 PEG monomers. According to one embodiment, the term miniPEG includes without limitation a —CH$_2$—(OCH$_2$—CH$_2$)$_q$OP$_1$ group where subscript q is an integer between 1-50 and P$_1$ is selected from the group consisting of H, (C$_1$-C$_8$)alkyl, (C$_2$-C$_8$)alkenyl, (C$_2$-C$_8$)alkynyl, (C$_3$-C$_8$)aryl, (C$_3$-C$_8$)cycloalkyl, (C$_3$-C$_8$)aryl(C$_1$-C$_6$) alkylene and (C$_3$-C$_8$)cycloalkyl(C$_1$-C$_6$)alkylene. Illustrative of miniPEG units include without limitation —CH$_2$—(OCH$_2$—CH$_2$)$_{1\text{-}45}$OH, —CH$_2$—(OCH$_2$—CH$_2$)$_{1\text{-}40}$OH, —CH$_2$—(OCH$_2$—CH$_2$)$_{1\text{-}35}$OH, —CH$_2$—(OCH$_2$—CH$_2$)$_{1\text{-}30}$OH, —CH$_2$—(OCH$_2$—CH$_2$)$_{1\text{-}25}$OH, —CH$_2$—(OCH$_2$—CH$_2$)$_{1\text{-}20}$OH, —CH$_2$—(OCH$_2$—CH$_2$)$_{1\text{-}15}$OH, —CH$_2$—(OCH$_2$—CH$_2$)$_{1\text{-}10}$OH, and —CH$_2$—(OCH$_2$—CH$_2$)$_{1\text{-}50}$H groups.

Further illustrative of the class minPEG are —CH$_2$—(OCH$_2$—CH$_2$)$_{1\text{-}45}$O(C$_1$-C$_8$)alkyl, —CH$_2$—(OCH$_2$—CH$_2$)$_{1\text{-}40}$O(C$_1$-C$_8$)alkyl, —CH$_2$—(OCH$_2$—CH$_2$)$_{1\text{-}35}$O(C$_1$-C$_8$)alkyl, —CH$_2$—(OCH$_2$—CH$_2$)$_{1\text{-}30}$O(C$_1$-C$_8$)alkyl, —CH$_2$—(OCH$_2$—CH$_2$)$_{1\text{-}25}$O(C$_1$-C$_8$)alkyl, —CH$_2$—(OCH$_2$—CH$_2$)$_{1\text{-}20}$O(C$_1$-C$_8$)alkyl, —CH$_2$—(OCH$_2$—CH$_2$)$_{1\text{-}15}$O(C$_1$-C$_8$)alkyl, —CH$_2$—(OCH$_2$—CH$_2$)$_{1\text{-}10}$O(C$_1$-C$_8$)alkyl, and —CH$_2$—(OCH$_2$—CH$_2$)$_{1\text{-}5}$O(C$_1$-C$_8$)alkyl groups.

"Alkyl" refers to straight, branched chain, or cyclic hydrocarbyl groups including from 1 to about 20 carbon atoms. For instance, an alkyl can have from 1 to 10 carbon atoms, 1-8 carbon atoms, or 1 to 5 carbon atoms. Exemplary alkyl includes straight chain alkyl groups such as methyl, ethyl, propyl, butyl, pentyl, hexyl, heptyl, octyl, nonyl, decyl, undecyl, dodecyl, and the like, and also includes branched chain isomers of straight chain alkyl groups, for example without limitation, —CH(CH$_3$)$_2$, —CH(CH$_3$) (CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH (CH$_2$CH$_3$)$_2$, —CH$_2$C(CH$_3$)$_3$, —CH$_2$C(CH$_2$CH$_3$)$_3$, —CH (CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$) CH$_2$CH(CH$_3$)$_2$, —CH(CH$_3$)CH(CH$_3$)CH(CH$_3$)$_2$, and the like. Thus, alkyl groups include primary alkyl groups, secondary alkyl groups, and tertiary alkyl groups.

The phrase "substituted alkyl" refers to alkyl substituted at 1 or more, e.g., 1, 2, 3, 4, 5, or even 6 positions, which substituents are attached at any available atom to produce a stable compound, with substitution as described herein. "Optionally substituted alkyl" refers to alkyl or substituted alkyl.

Each of the terms "halogen," "halide," and "halo" refers to —F, —Cl, —Br, or —I.

The terms "alkylene" and "substituted alkylene" refer to divalent alkyl and divalent substituted alkyl, respectively. Examples of alkylene include without limitation, ethylene (—CH$_2$—CH$_2$—). "Optionally substituted alkylene" refers to alkylene or substituted alkylene.

"Alkene or alkenyl" refers to straight, branched chain, or cyclic hydrocarbyl groups including from 2 to about 20 carbon atoms having one or more carbon to carbon double bonds, such as 1 to 3, 1 to 2, or at least one carbon to carbon double bond. "Substituted alkene" refers to alkene substituted at 1 or more, e.g., 1, 2, 3, 4, 5, or even 6 positions, which substituents are attached at any available atom to produce a stable compound, with substitution as described herein. "Optionally substituted alkene" refers to alkene or substituted alkene.

The term "alkenylene" refers to divalent alkene. Examples of alkenylene include without limitation, ethenylene (—CH═CH—) and all stereoisomeric and conformational isomeric forms thereof. "Substituted alkenylene" refers to divalent substituted alkene. "Optionally substituted alkenylene" refers to alkenylene or substituted alkenylene.

"Alkyne or "alkynyl" refers to a straight or branched chain unsaturated hydrocarbon having the indicated number of carbon atoms and at least one triple bond. Examples of a (C$_2$-C$_8$)alkynyl group include, but are not limited to, acetylene, propyne, 1-butyne, 2-butyne, 1-pentyne, 2-pentyne, 1-hexyne, 2-hexyne, 3-hexyne, 1-heptyne, 2-heptyne, 3-heptyne, 1-octyne, 2-octyne, 3-octyne and 4-octyne. An alkynyl group can be unsubstituted or optionally substituted with one or more substituents as described herein below.

The term "alkynylene" refers to divalent alkyne. Examples of alkynylene include without limitation, ethynylene, propynylene. "Substituted alkynylene" refers to divalent substituted alkyne.

The term "alkoxy" refers to an —O-alkyl group having the indicated number of carbon atoms. For example, a (C$_1$-C$_6$)alkoxy group includes —O-methyl (methoxy), —O-ethyl (ethoxy), —O-propyl (propoxy), —O-isopropyl (isopropoxy), —O-butyl (butoxy), —O-sec-butyl (sec-butoxy), —O-tert-butyl (tert-butoxy), —O-pentyl (pentoxy), —O-isopentyl (isopentoxy), —O— neopentyl (neopentoxy), —O-hexyl (hexyloxy), —O-isohexyl (isohexyloxy), and —O-neohexyl (neohexyloxy).

"Hydroxyalkyl" refers to a (C$_1$-C$_{10}$)alkyl group wherein one or more of the alkyl group's hydrogen atoms is replaced with an —OH group. Examples of hydroxyalkyl groups include, but are not limited to, —CH$_2$OH, —CH$_2$CH$_2$OH, —CH$_2$CH$_2$CH$_2$OH, —CH$_2$CH$_2$CH$_2$CH$_2$OH, —CH$_2$CH$_2$CH$_2$CH$_2$CH$_2$OH, —CH$_2$CH$_2$CH$_2$CH$_2$CH$_2$CH$_2$OH, and branched versions thereof.

The term "ether" or "oxygen ether" refers to (C$_1$-C$_{10}$) alkyl group wherein one or more of the alkyl group's carbon atoms is replaced with an —O— group. The term ether includes —CH$_2$—(OCH$_2$—CH$_2$)$_q$OP1 compounds where P1 is a protecting group, —H, or a (C$_1$-C$_{10}$)alkyl. Exemplary ethers include polyethylene glycol, diethylether, methylhexyl ether and the like.

The term "thioether" refers to (C$_1$-C$_{10}$)alkyl group wherein one or more of the alkyl group's carbon atoms is replaced with an —S— group. The term thioether includes —CH$_2$—(SCH$_2$—CH$_2$)$_q$—SP$_1$ compounds where P1 is a protecting group, —H, or a (C$_1$-C$_{10}$)alkyl. Exemplary ethers include dimethylthioether, ethylmethyl thioether.

The term "aryl," alone or in combination refers to an aromatic monocyclic or bicyclic ring system such as phenyl or naphthyl. "Aryl" also includes aromatic ring systems that are optionally fused with a cycloalkyl ring as herein defined.

A "substituted aryl" is an aryl that is independently substituted with one or more substituents attached at any available atom to produce a stable compound, wherein the substituents are as described herein. "Optionally substituted aryl" refers to aryl or substituted aryl.

"Arylene" denotes divalent aryl, and "substituted arylene" refers to divalent substituted aryl. "Optionally substituted arylene" refers to arylene or substituted arylene.

The term "heteroatom" refers to N, O, and S. Inventive compounds that contain N or S atoms can be optionally oxidized to the corresponding N-oxide, sulfoxide or sulfone compounds.

The term "cycloalkyl" refer to monocyclic, bicyclic, tricyclic, or polycyclic, 3- to 14-membered ring systems, which are either saturated, unsaturated or aromatic. The cycloalkyl group may be attached via any atom. Cycloalkyl also contemplates fused rings wherein the cycloalkyl is fused to an aryl or hetroaryl ring as defined above. Representative examples of cycloalkyl include, but are not limited to cyclopropyl, cyclobutyl, cyclopentyl, and cyclohexyl. A cycloalkyl group can be unsubstituted or optionally substituted with one or more substituents as described herein below.

The term "cycloalkylene" refers to divalent cycloalkyl. The term "optionally substituted cycloalkylene" refers to cycloalkylene that is substituted with 1 to 3 substituents, e.g., 1, 2 or 3 substituents, attached at any available atom to produce a stable compound, wherein the substituents are as described herein.

The term 'nitrile or cyano" can be used interchangeably and refer to a —CN group which is bound to a carbon atom of a heteroaryl ring, aryl ring and a heterocycloalkyl ring.

The term "oxo" refers to a ═O atom attached to a saturated or unsaturated (C$_3$-C$_8$) cyclic or a (C$_1$-C$_8$) acyclic moiety. The ═O atom can be attached to a carbon, sulfur, and nitrogen atom that is part of the cyclic or acyclic moiety.

The term "amine or amino" refers to an —NR$^d$R$^e$ group wherein R$^d$ and R$^e$ each independently refer to a hydrogen, (C$_1$-C$_8$)alkyl, aryl, heteroaryl, heterocycloalkyl, (C$_1$-C$_5$) halo alkyl, and (C$_1$-C$_6$)hydroxyalkyl group.

The term "amide" refers to a —NR'R"C(O)— group wherein R and R" each independently refer to a hydrogen, (C$_1$-C$_8$)alkyl, or (C$_3$-C$_6$)aryl.

A "hydroxyl" or "hydroxy" refers to an —OH group.

The term "(C$_3$-C$_8$)aryl-(C$_1$-C$_6$)alkylene" refers to a divalent alkylene wherein one or more hydrogen atoms in the C$_1$-C$_6$ alkylene group is replaced by a (C$_3$-C$_8$)aryl group. Examples of (C$_3$-C$_8$)aryl-(C$_1$-C$_6$)alkylene groups include without limitation 1-phenylbutylene, phenyl-2-butylene, 1-phenyl-2-methylpropylene, phenylmethylene, phenylpropylene, and naphthylethylene.

The term "(C$_3$-C$_8$)cycloalkyl-(C$_1$-C$_6$)alkylene" refers to a divalent alkylene wherein one or more hydrogen atoms in the C$_1$-C$_6$ alkylene group is replaced by a (C$_3$-C$_8$)cycloalkyl group. Examples of (C$_3$-C$_8$)cycloalkyl-(C$_1$-C$_6$)alkylene groups include without limitation 1-cyproylbutylene, cyloproyl-2-butylene, cyclopentyl-1-phenyl-2-methylpropylene, cyclobutylmethylene and cyclohexylpropylene.

A "peptide nucleic acid" refers to a DNA or RNA mimic in which the sugar phosphodiester backbone of the DNA or RNA is replaced by a N-(2-aminoethyl)glycine unit.

Some compounds described here can have asymmetric centers and therefore exist in different enantiomeric and diastereomeric forms. A compound of the invention can be in the form of an optical isomer or a diastereomer. Accordingly, the invention encompasses compounds of the invention and their uses as described herein in the form of their optical isomers, diastereoisomers and mixtures thereof, including a racemic mixture. Optical isomers of the compounds of the invention can be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

Compounds

The γ-PNA monomers of the present invention are conformationally preorganized ethylene glycol containing compounds according to Formula I.

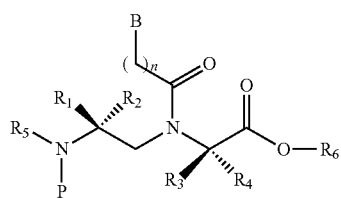

For Formula I compounds, B is a nucleic acid base selected from adenine, guanine, cytosine, thymine or uracil.

Each of groups $R_1$, $R_2$ and $R_5$ are independently selected from the group consisting of H, linear or branched $(C_1\text{-}C_8)$ alkyl, $(C_2\text{-}C_8)$alkenyl, $(C_2\text{-}C_8)$alkynyl, $(C_3\text{-}C_8)$aryl, $(C_3\text{-}C_8)$ cycloalkyl, $(C_3\text{-}C_8)$aryl$(C_1\text{-}C_6)$alkylene, $(C_3\text{-}C_8)$cycloalkyl $(C_1\text{-}C_6)$alkylene, $-CH_2-(OCH_2-CH_2)_q OP1$, $-CH_2-(OCH_2-CH_2)_q-NHP1$, $-CH_2-(OCH_2-CH_2)_q-SP_1$ and $-CH_2-(SCH_2-CH_2)_q-SP_1$. According to one embodiment, $R_1$ and $R_2$ are each independently $-CH_2-(OCH_2-CH_2)_q OP1$. For instance, $R_1$ can be a $-CH_2-(OCH_2-CH_2)_q OP1$ group and $R_2$ can be selected from the group consisting of H, linear or branched $(C_1\text{-}C_8)$alkyl, $(C_2\text{-}C_8)$alkenyl, $(C_2\text{-}C_8)$alkynyl, $(C_3\text{-}C_8)$aryl, $(C_3\text{-}C_8)$cycloalkyl, $(C_3\text{-}C_8)$aryl$(C_1\text{-}C_6)$alkylene, $(C_3\text{-}C_8)$cycloalkyl $(C_1\text{-}C_6)$alkylene, $-CH_2-(OCH_2-CH_2)_q-NHP1$, $-CH_2-(OCH_2-CH_2)_q-SP_1$ and $-CH_2-(SCH_2-CH_2)_q-SP_1$. In one embodiment, $R_1$ is a $-CH_2-(OCH_2-CH_2)_q OH$ group and subscript q is an integer between 1-25 both integers inclusive, between 1-20 both integers inclusive, between 1-15 both integers inclusive and between 1-10 both integers inclusive.

According to one embodiment, the present invention provides Formula I compounds in which each of groups $R_3$ and $R_4$ independently is H. For Formula I compounds $R_6$ is selected from the group consisting of H, linear or branched $(C_1\text{-}C_8)$alkyl, substituted or unsubstituted $(C_3\text{-}C_8)$aryl and $(C_3\text{-}C_8)$aryl$(C_1\text{-}C_6)$alkylene.

Substituent P on the terminal amino group of a Formula I compound can be hydrogen or an amine protecting group. Exemplary of such protecting groups include without limitation 9-fluorenylmethyloxy carbonyl (Fmoc), t-butyloxycarbonyl (Boc), benzhydryloxycarbonyl (Bhoc), benzyloxycarbonyl (Cbz), O-nitroveratryloxycarbonyl (Nvoc), benzyl (Bn), allyloxycarbonyl (alloc), trityl (Trt), 1-(4,4-dimethyl-2,6-dioxacyclohexylidene)ethyl (Dde), diathiasuccinoyl (Dts), benzothiazole-2-sulfonyl (Bts), dimethoxytrityl (DMT) and monomethoxytrityl (MMT) group.

For certain Formula I compounds substituent $P_1$ is selected from the group consisting of H, $(C_1\text{-}C_8)$alkyl, $(C_2\text{-}C_8)$alkenyl, $(C_2\text{-}C_8)$alkynyl, $(C_3\text{-}C_8)$aryl, $(C_3\text{-}C_8)$cycloalkyl, $(C_3\text{-}C_8)$aryl$(C_1\text{-}C_6)$alkylene and $(C_3\text{-}C_8)$cycloalkyl $(C_1\text{-}C_6)$alkylene. Subscripts n and q In Formula I are independently integers between 0 and 50 both integers inclusive. According to one embodiment, subscript n is 1 while subscript p is an integer between 1-45, preferably between 1-40, 1-35, 1-30, 1-25, 1-20, 1-15, or 1-10.

According to one embodiment, the compound of formula I is as shown in Chart 1:

CHART 1

Chemical compositions of the inventions.

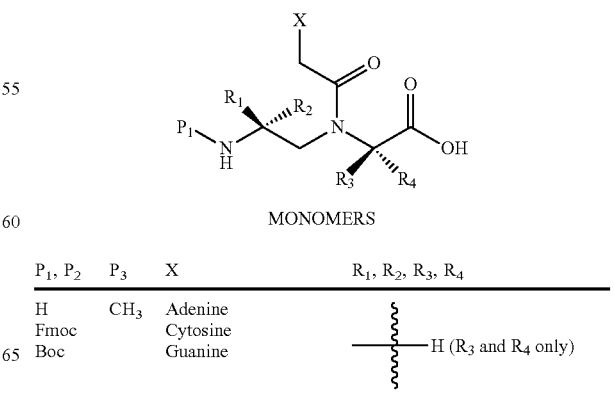

MONOMERS

| $P_1$, $P_2$ | $P_3$ | X | $R_1$, $R_2$, $R_3$, $R_4$ |
|---|---|---|---|
| H | $CH_3$ | Adenine | |
| Fmoc | | Cytosine | |
| Boc | | Guanine | H ($R_3$ and $R_4$ only) |

CHART 1-continued

Chemical compositions of the inventions.

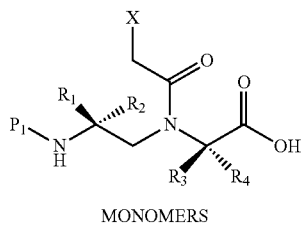

MONOMERS

| $P_1, P_2$ | $P_3$ | X | $R_1, R_2, R_3, R_4$ |
|---|---|---|---|
| Cbz
Bn | | Thymine
Modified nucleobases | —CH$_2$[O(CH$_2$)$_2$]$_{1-10}$OP$_3$ |
| Tos
Alloc | | Fluorophores
Aromatic ligands | —CH$_2$[O(CH$_2$)$_2$]$_{1-10}$NP$_2$ |
| Trt
MMT
DMT | | | —CH$_2$[O(CH$_2$)$_2$]$_{1-10}$SP$_2$ |

Compounds conforming to Formula I are chiral by virtue of substituent group diversity at C-γ. A typical stereomerically pure Formula I compound comprises greater than about 80% by weight of one stereoisomer of the compound and less than about 20% by weight of other stereoisomers of the compound. According to an embodiment, a stereomerically pure Formula I compound comprises greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound or greater than or equal to about 99% by weight of one stereoisomer of the compound and less than or equal to about 1% by weight of the other stereoisomer respectively.

While MP and larger molecular-weight polyethylene glycol (PEG) units have been incorporated into a number of macromolecular systems including, for example, peptides and proteins, nucleic acids, carbohydrates, synthetic polymers, dendrimers, liposomes, and nanoparticles, the present inventors unexpectedly found that the introduction of a diethylene glycol group, commonly referred to as 'miniPEG' or MP, in the backbone of PNA enhanced the aqueous solubility, biocompatibility and binding specificity along with reduction in aggregation and nonspecific binding of the PNA.

The PNA backbone offers a choice of three sites (C-α, C-β and C-γ), for introducing a miniPEG (MP) group. Previous studies by the present inventors have indicated that installation of a chiral center at position C-γ within the PNA backbone induces helical organization (helicity) in the oligomer and provides a means for fine-tuning the thermodynamic stability of PNAs. The helical conformation adopted by an oligomer containing PNA monomers depends in part on the stereochemistry of the PNA monomers used. Two helical conformations are possible, namely, a right-handed conformation and a left-handed conformation. γPNAs prepared from L-amino acids adopt a right-handed helix, while those prepared from D-amino acids adopt a left-handed helix. However, bioanalytical studies indicate that only the right-handed helical γPNAs hybridize to DNA and RNA with high affinity and sequence selectivity.

Synthesis

A. General Synthetic Protocols

Figure 7:
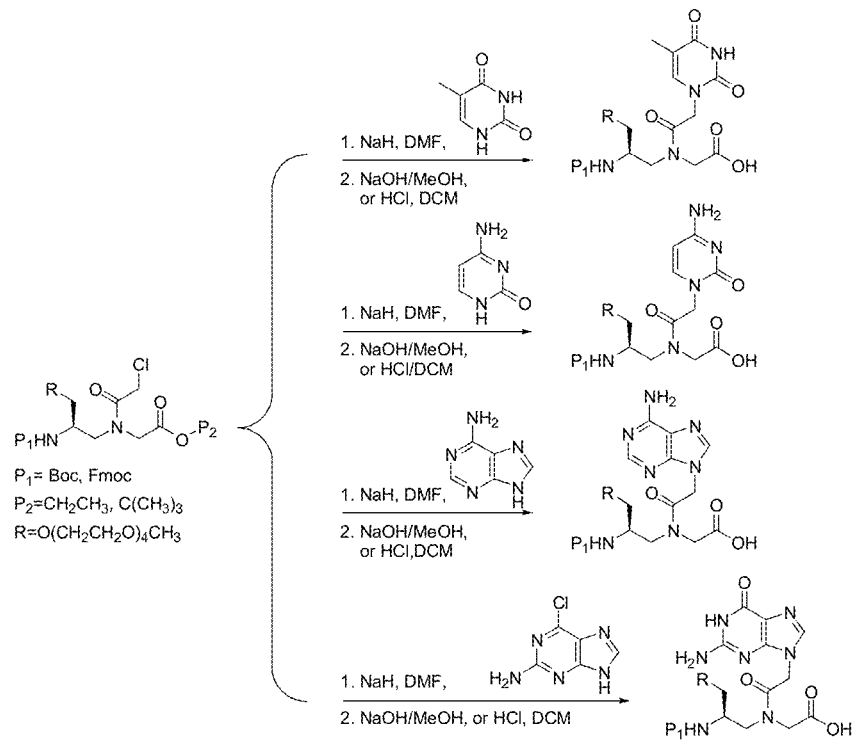
FIG. 7 illustrates a synthetic reaction scheme that does not require protection of nucleobases, wherein unprotected nucleobases are directly coupled to a Boc- or a Fmoc-protected γPNA backbone.

Traditional routes for synthesizing PNAs have been tedious, involving the preparation of protected nucleobases—A, C, and G, and the use of toxic chemicals and multiple steps to obtain an orthogonally protected PNA monomer that can be used for synthesizing oligomers using a resin. As illustrated in FIG. 7, the present inventors have developed synthetic methodologies that do not require protection of nucleobases. Rather, PNA monomers according to Formula I are readily prepared using cheap, commercially available, unprotected nucleobases that are directly coupled to a Boc- or a Fmoc-protected γPNA backbone.

Figure 8:
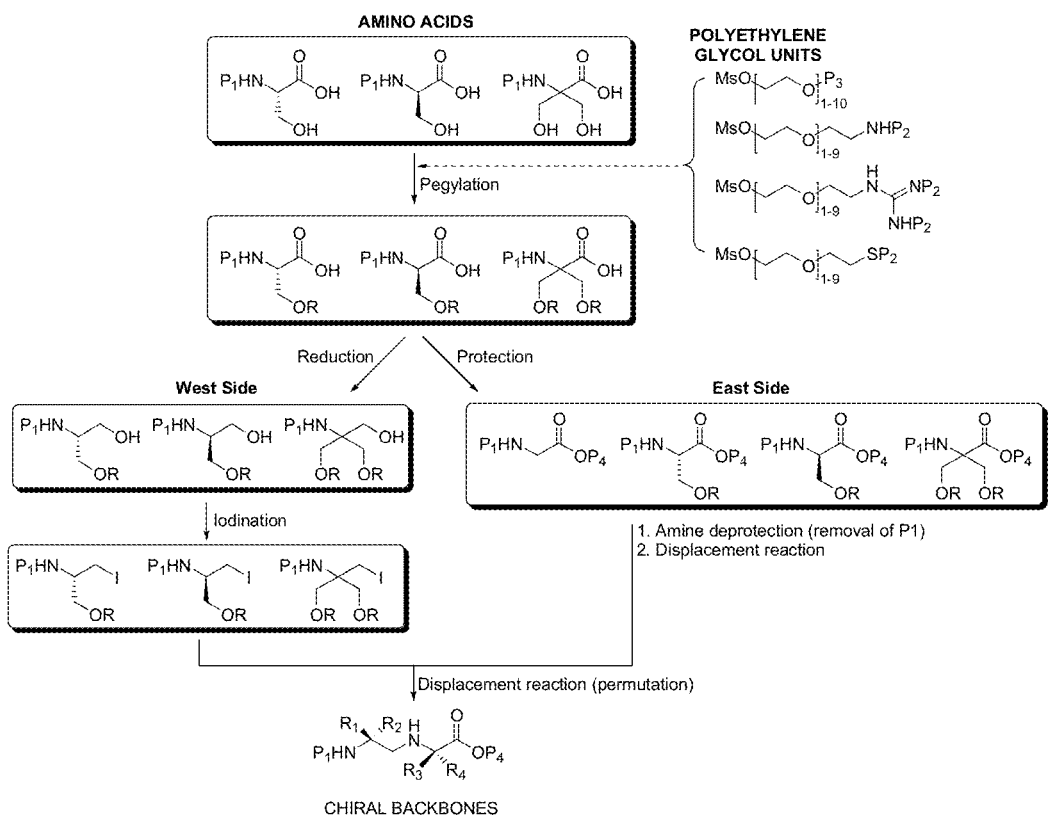
FIG. 8 illustrates an efficient method for synthesizing the Boc-protected and/or Fmoc-protected PNA backbones, using Boc- and Fmoc-protected amino acids, for example, Boc or Fmoc protected alanine, threonine, cysteine, or serine.

Also provided is an efficient method for synthesizing the Boc-protected and/or Fmoc-protected PNA backbones. Compared to the traditional Mitsunobu synthetic route used in the preparation of PNA backbones, synthesis of PNA backbones according to the methods described herein is accomplished in a few simple steps from commercially available and relatively cheap Boc- and Fmoc-protected amino acids, for example, Boc or Fmoc protected alanine, threonine, cysteine, or serine according to the protocol (FIG. 8). Following this method, no elaborate column chromatography purification is necessary to obtain PNA backbones that have the required purity for coupling to unprotected nucleobases.

Figure 9:
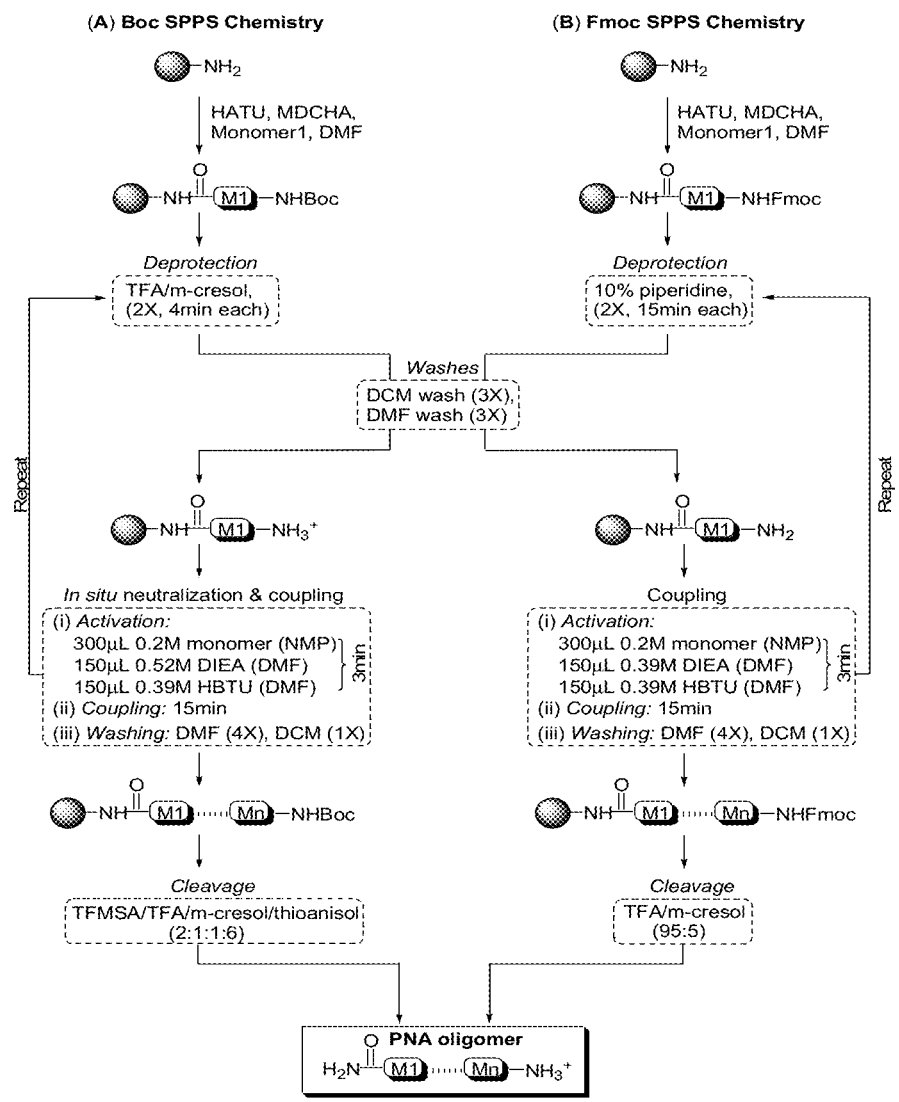
FIG. 9 illustrates a solid phase synthesis for Formula I PNA monomers using Boc-protected (pathway (A)) and Fmoc-protected PNA (pathway (B)) monomers.

The present invention also provides an optimized solid-phase reaction sequence for synthesizing PNA containing oligomers that is more efficient and reduces or eliminates a number of hazardous chemical transformation steps that routinely accompany traditional solid phase synthesis (FIG. 9). Synthetic methodologies described herein, have led to significant cost-reductions in the production of γPNA monomers and oligomers.

The synthetic protocol illustrated in FIG. 9 is optimized to efficiently couple PNA monomers according to Formula I to a solid resin support with minimal side-reactions (less than 1%) or cross-coupling reactions between the unprotected, exocyclic amino groups of adenine, cytosine, or guanine nucleobase and the activated carboxyl group of a PNA monomer. Because solid phase synthesis according to the inventive protocol uses unprotected nucleobases no deprotection of the nucleobases in the final oligomer product are necessary prior to cleavage of the oligomer from the solid support. Additionally, pyridine neutralization and capping steps necessary for solid phase synthesis of DNA or RNA oligomers using conventional methods are omitted in the present method with no effect on the overall yield or purity of the final MP-γPNA oligomers.

Bypassing these steps not only significantly reduces the synthesis time, but also reduces the costs of oligomer synthesis and costs associated with disposal of hazardous wastes, such as pyridine and acetic anhydride, omitted from the protocol shown in FIG. 9.

FIG. 9 illustrates a solid phase synthesis for Formula I PNA monomers using Boc-protected ((A) Boc SPPS Chemistry) and Fmoc-protected PNA monomers ((B) Fmoc SPPS Chemistry). As stated above, one advantage of carrying out oligomer synthesis using a solid support is that it permits in situ neutralization of the ammonium ion generated by trifluoroacetic acid (TFA) cleavage of the Boc protecting group.

According to the present inventors in situ neutralization is superior to the standard, pyridine wash/neutralization sequence used conventionally because it improves the overall yield and purity of MP-γPNA oligomers.

Another advantage of the synthetic method according to the present invention is the use of a C-terminal thioester activated PNA monomer in coupling reactions. Traditional synthetic routes do not employ C-terminal thioester monomers for synthesis because of the ensuing intramolecular esterification and N-terminal truncation. In contrast, oligomer synthesis using a method according to the present invention does not suffer from these drawbacks. This is so because neutralization of the ammonium ion is carried out in situ and also due the greater rigidity of the γ-modified PNA oligomers than their achiral counterparts. Enhanced oligomer rigidity disfavors intramolecular esterification and N-terminal truncation products.

Figure 10A:
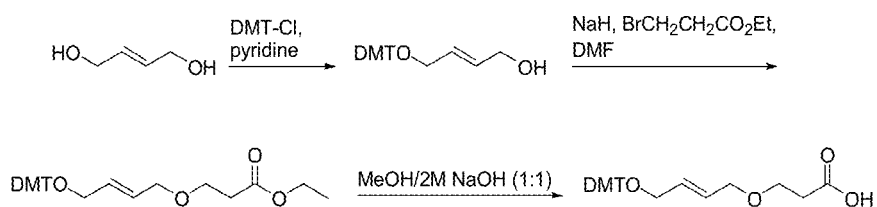
FIGS. 10A and 10B illustrates the use of a novel allyl linker to connect the first PNA building block to a solid resin support (FIG. 10A), and release of the final oligomer from the solid support under near neutral conditions by treating the resin with palladium tetrakis triphenylphosphine (Pd (PPh$_3$)$_4$) and a stoichiometric amount of morpholine (FIG. 10B).
Figure 10B:
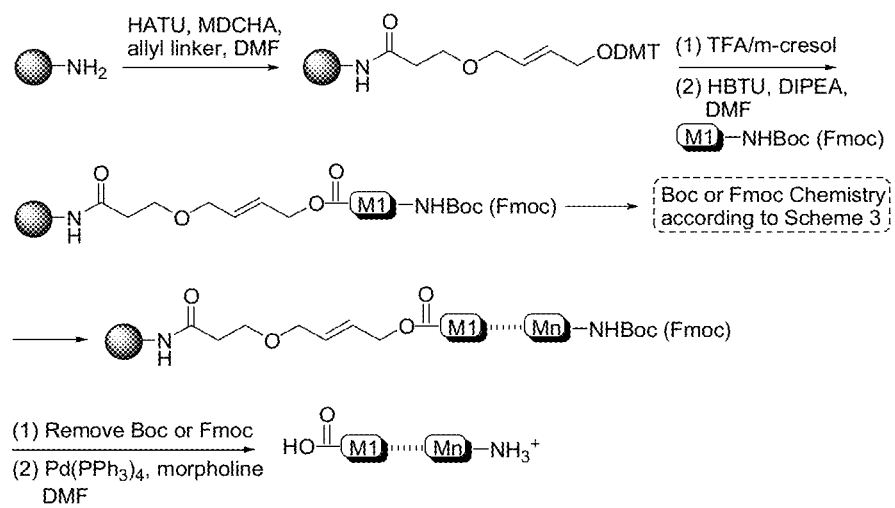

As stated above, the use of PNA monomers that have unprotected nucleobases during solid phase synthesis of an oligomer permits cleavage of the oligomer product from the resin support under mild conditions. According to one embodiment, the inventors have developed a novel allyl linker to connect the first PNA building block to the solid resin support. See FIG. 10A. The main advantage of the allyl linker is that it permits the release of the final oligomer from the solid support under near neutral conditions by treating the resin with palladium tetrakis triphenylphosphine (Pd (PPh$_3$)$_4$) and stoichiometric amount of morpholine (FIG. 10B).

PNA oligomers are important molecular tools in analytical assays and as therapeutic and diagnostic reagents for the treatment and detection of genetic diseases. Many diagnostic assays rely on sequence specific hybridization of the PNA oligomer to single stranded or duplex DNA or RNA. Other assays use a chemical probe covalently attached to the PNA oligomer to detect a biological macromolecule of interest. Both assay methods rely on the subsequent release of the PNA-DNA or PNA-RNA hybrid, or the release of the probe-biological macromolecule complex from the solid surface to permit their detection and quantitation.

Reagents traditionally used to release the PNA complexes from the solid support, however, are harsh and unsuitable for use with many biological samples. The present inventors have addressed this problem by developing a novel allyl linker to attach PNA oligomers to a solid support so as to facilitate the gentle release of the PNA-biocomplex formed during the assay under near neutral conditions.

B. Synthesis of Specific γPNA Monomers

Figure 11:
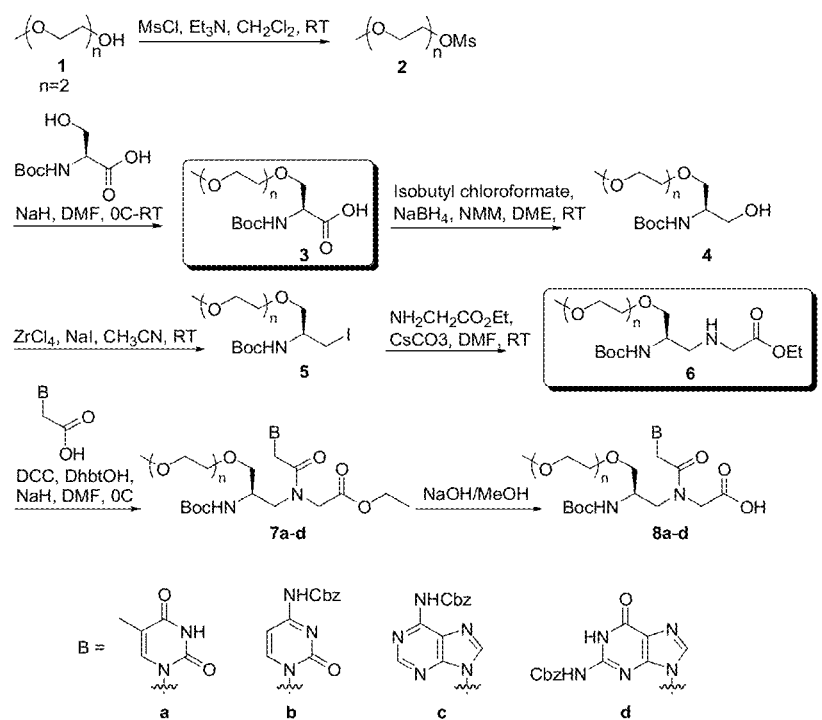
FIG. 11 illustrates the synthesis of Boc-protected $^{R\text{-}MP}$γPNA monomers containing all four natural nucleobases (A, C, G, T).

In one embodiment, Boc-protected $^{R\text{-}MP}$γPNA monomers containing all four natural nucleobases (A, C, G, T) were synthesized according to the procedures outlined in FIG. 11.

As illustrated in FIG. 11, alkylation of Boc-protected L-serine (1) with 1-bromo-2-(2-methoxyethoxy)ethane or 2-(2-methoxyethoxy)ethane methane sulfonate (2) was carried out as follows. To a vigorously stirred, chilled solution of DMF containing 2 equivalents of sodium hydride was slowly added compound (1), followed by addition of 1-bromo-2-(2-methoxyethoxy)ethane or or 2-(2-methoxyethoxy)ethane methane sulfonate (2). After stirring at 0° C. for 1 hr, the mixture was quenched by addition of water at 0° C. The solvents (DMF and water) were removed under reduced pressure at room temperature. Water was added to the crude mixture and the pH was adjusted to ~3 using 5% HCl. The aqueous solution was extracted with ethyl acetate and dried over Na$_2$SO$_4$. The resultant product is pegylated Boc-protected serine, compound 3 which is obtained with high optical purity.

Both the stoichiometry and order of addition of reagents were determined to be important for obtaining an optically pure product. Slow addition of Boc-serine is necessary to ensure complete deprotonation of the carboxyl group prior to removal of the hydroxyl proton. Formation of the carboxylate anion reduces the acidity of the α-proton making it less susceptible to deprotonation by base.

Esterification of the alkylated product (3) followed by reduction with sodium borohydride yields the corresponding alcohol, serinol (4). The conversion of the carboxylic acid moiety to an alcohol renders the Cα-proton inert to deprotonation and racemization in subsequent reaction steps. The serinol (4) was allowed to react with sodium iodide in the presence of zirconium (IV) chloride (ZrCl$_4$) as a catalyst to obtain the corresponding iodide (5). Subsequent displacement of the iodide by ethyl glycinate yielded the PNA backbone (6).

Dicyclohexylcarbodiimide (DCC) mediated coupling of 6 with the appropriate carboxymethylnucleobases (A, C, G, and T), followed by hydrolysis of the resulting ester group gave the desired Formula I γPNA monomers (8a-d).

The optical purities of key intermediates and final γPNA monomers according to Formula I were determined by $^{19}$F-NMR following chemical derivatization as described in the literature. See Seco et al., *Chem. Rev.* 2004, 104, 17-117. Gas chromatography coupled to mass spectrometric detection (GC/MS) has been described in the literature to determine the enantiomeric excess (ee) of chiral α-PNA monomers and their oligomers. See Corradini et al., *Tetrahedron: Asymmetry* 1999, 10, 2063-2066.

The present inventors found $^{19}$F-NMR to be a convenient and accurate alternative method for determining the ee values for Formula I γPNA monomers and synthetic intermediates of γPNA monomers. Analysis by $^{19}$F-NMR required removal of the Boc-protecting group and subsequent coupling of the free amine group of a Formula I γPNA monomer a synthetic intermediate of γPNA monomer with (+)-1-methoxy-1-(trifluoromethyl)phenylacetyl chloride (MTPA-Cl, Mosher's reagent).

Boc-D-serine was used as the starting reagent to synthesize the corresponding PNA stereoisomer ($^{S\text{-}MP}$γPNA monomer), which is required as a control to quantify the enantiomeric excess of the desired $^{R\text{-}MP}$γPNA monomer. Inspection of the $^{19}$F-NMR spectral trace for MTPA derivatized $^{R\text{-}MP}$γPNA monomer and $^{S\text{-}MP}$γPNA monomer revealed no traces of the $^{S\text{-}MP}$γPNA monomer indicating that the desired Formula I compound is optically pure. Based on the spectral data it was concluded that the desired Formula I PNA monomer had an optical purity of 99% ee, within the detection limit of $^{19}$F-NMR.

While thymine $^{R\text{-}MP}$γPNA monomer showed two peaks for rotamers at −68.80 and −68.95 ppm in the NMR spectrum, the corresponding thymine $^{S\text{-}MP}$γPNA showed only one rotamer. The existence of the two rotamers for thymine $^{R\text{-}MP}$γPNA monomer is unclear.

γPNA monomers manufactured according to synthetic protocols described above have enantiomeric purity of at least 90% by weight of one stereoisomer of the compound and less than about 10% by weight of the other stereoisomer of the compound, or greater than about 95% by weight of one stereoisomer of the compound and less than about 5% by weight of the other stereoisomer of the compound, or greater than about 97% by weight of one stereoisomer of the compound and less than about 3% by weight of the other stereoisomer of the compound or greater than or equal to about 99% by weight of one stereoisomer of the compound and less than or equal to about 1% by weight of the other stereoisomer respectively.

$^{R\text{-}MP}\gamma$PNA monomers based on the L-alanine scaffold were synthesized as described by Rapireddy et al., *J. Am. Chem. Soc.* 2007, 129, 15596-15600 and He et al., *J. Am. Chem. Soc.* 2009, 131, 12088-12090.

While L-alanine-derived γPNA ($^{S\text{-}Ala}\gamma$pNA) oligomers are able to invade mixed-sequence double helical B-form DNA (B-DNA) and are promising as antisense and antigene reagents, the $^{S\text{-}Ala}\gamma$PNAs are poorly soluble in water and have a tendency to aggregate, presumably due to the charge-neutral backbone and hydrophobic character of the γ-Me. According to one embodiment, therefore, the replacement of the side chain methyl group with miniPEG, for example, an ethylene glycol unit $[(OCH_2CH_2)_n$, where n=1-10] at C-γ results in a (R)miniPEG PNA monomer according to Formula I. Introducing the (R)miniPEG PNA monomer into a oligomer chain induces a right-handed helix in the resultant PNA oligomer. Such oligomers have improved water solubility and reduced aggregation while retaining superior hybridization properties.

Biochemical Analysis

To evaluate whether a PNA oligomer containing one or more γPNA monomers according to Formula I influence the conformation and hybridization properties of PNA oligomer or influence the water solubility and aggregation properties of a PNA oligomer, the present inventors synthesized PNA oligomers whose sequences are shown in Table 1 below.

TABLE 1

Sequence of PNA oligomers

| Oligo-mer | Sequence | #MP units | SEQ ID NO: |
|---|---|---|---|
| PNA1 | H-GCATGTTTGA-NH$_2$ | 0 | 1 |
| PNA2 | H-GCATGTTTGA-NH$_2$ | 1 | 2 |
| PNA3 | H-GCATGTTTGA-NH$_2$ | 3 | 3 |
| PNA4 | H-GCATGTTTGA-NH$_2$ | 5 | 4 |
| PNA5 | H-GCATGTTTGA-NH$_2$ | 10 | 5 |
| PNA6 | H-ACGGGTAGAATAACAT-NH$_2$ | 0 | 6 |
| PNA7 | H-ACGGGTAGAATAACAT-NH$_2$ | 1 | 7 |
| PNA8 | H-ACGGGTAGAATAACAT-NH$_2$ | 3 | 8 |
| PNA9 | H-ACGGGTAGAATAACAT-NH$_2$ | 5 | 9 |
| PNA10 | H-ACGGGTAGAATAACAT-NH$_2$ | 8 | 10 |
| PNA1X | H-$^L$Orn(X)-$^L$Lys-GCATGTTTGA-NH$_2$ | 0 | 1 |
| PNA1Y | H-$^L$Lys-GCATGTTTGA-$^L$Orn(Y)-NH$_2$ | 0 | 1 |
| PNA4X | H-$^L$Orn(X)-$^L$Lys-GCATGTTTGA-NH$_2$ | 5 | 4 |
| PNA4Y | H-$^L$Lys-GCATGTTTGA-$^L$Orn(Y)-NH$_2$ | 5 | 4 |

Underlined letter indicates R-MP-γ-backbone modification. X = fluorescein (FITC), Y = tetramethylrhodamine (TAMRA).

The first set of oligomers (PNA1 through 5), were designed to test the effects of miniPEG on the conformation and hybridization properties of PNA. The second set of oligomers (PNA6 through 10), was designed to test the effect of miniPEG on water solubility. A hexadecameric sequence is chosen for the aqueous solubility study because such a sequence represents a statistical length that would be required to target a unique site within the mammalian genome or transcriptome. The third set included two oligomers (PNA1 and 4). Each oligomer in this set was designed to test the effect of miniPEG on self-aggregation tendency of PNA containing oligomers using Førster Resonance Energy Transfer (FRET). Thus, PAN's 1 and 4 were separately linked to fluorescein (FITC) at the N-terminus (PNA1X and PNA4X) and tetramethylrhodamine (TAMRA) group at the C-terminus (PNA1Y and PNA4) of each oligomer. A lysine residue was introduced at the C-terminus to improves water-solubility and aid in the purification and characterization of the labeled oligomerss.

All PNA oligomers, those with and without MP sidechains, are synthesized on solid-support according to the protocols described herein or published in the literature. Unlike PNA's with modifications made at the α-backbone that require further optimization of the solid phase resin reaction coupling conditions in order to minimize racemization, no precautions or modification of the synthetic protocol are necessary for coupling of the inventive Formula I $^{R\text{-}MP}\gamma$PNA monomers on the resin.

Moreover, after coupling the last monomer the resultant oligomer can be readily cleaved from the resin and precipitated with ethyl ether. The air-dried pellets of the crude oligomers are dissolved in water/acetonitrile mixture (80/20), and purified by reverse-phase HPLC and characterized by MALDI-TOF mass spectrometry.

1. Effect of MiniPEG of Oligomer Conformation & Hybridization

PNA1 through 5 oligomers were analyzed by CD spectroscopy to determine the effect of minPEG on the conformation of PNA oligomers. Consistent with the earlier findings (Dragulescu-Andrasi, A. et al.; *J. Am. Chem. Soc.* 2006, 128, 10258-10267), no CD signals were observed within the nucleobase absorption regions for PNA1 that does not contain a Formula I R-MP-γPNA group. See FIG. 1A. This observation indicates that this PNA oligomer either (i) does not adopt a helical conformation, or (ii) has an equal proportion of a right-handed and left-handed helix in the analytical sample.

Figure 3:
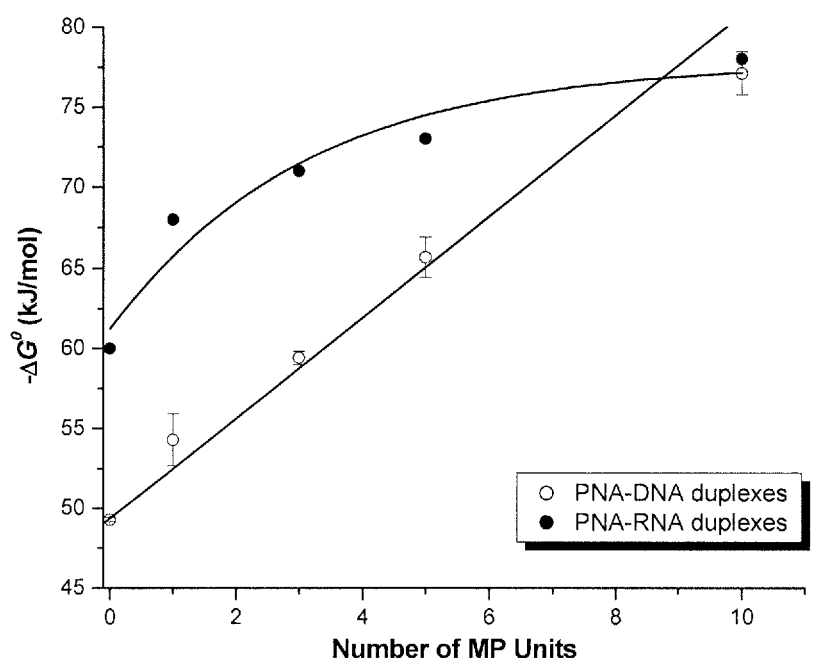
FIG. 3 illustrates the correlation between Gibbs binding free energy (ΔG°) and the number of miniPEG units in PNA-DNA and PNA-RNA duplexes.

However, PNA2 through 5 show distinct exciton coupling patterns in the CD spectrum with two distinct minima's at 242 and 280 nm and two maxima's at 220 and 260 nm. The observed CD pattern is characteristic of a right-handed helix. See FIG. 3B. The addition of miniPEG units did not alter the amplitude of the CD signals. However, the addition of miniPEG does alter the wavelengths of maxima and minima, shifting it towards that of the PNA-DNA and PNA-RNA double helices (FIG. 3B).

Moreover, a gradual dip at the 242 nm minimum generally indicates a tightening in the helical pitch of the oligomer from one that resembles that of a PNA-PNA duplex with 18 base-pairs per turn to one that resembles that of a PNA-DNA duplex with 13 base-pairs per turn. Overall, the CD profiles of PNA2 through 5 are similar to those of the corresponding PNA-DNA and PNA-RNA hybrid duplexes (FIG. 3B), the major difference in the CD trace being the amplitude which is roughly doubled for the duplex as compared to individual PNA strand.

Without ascribing to a particular theory, this doubling of amplitude is likely due to the higher concentration of bases in the hybrid duplex (approximately twice the concentration), than that of the individual PNA strand. Taken together, these results show that a single, (R)-MP unit installed at the γ-backbone is sufficient to preorganize PNA into a right-handed helix.

Figure 4:
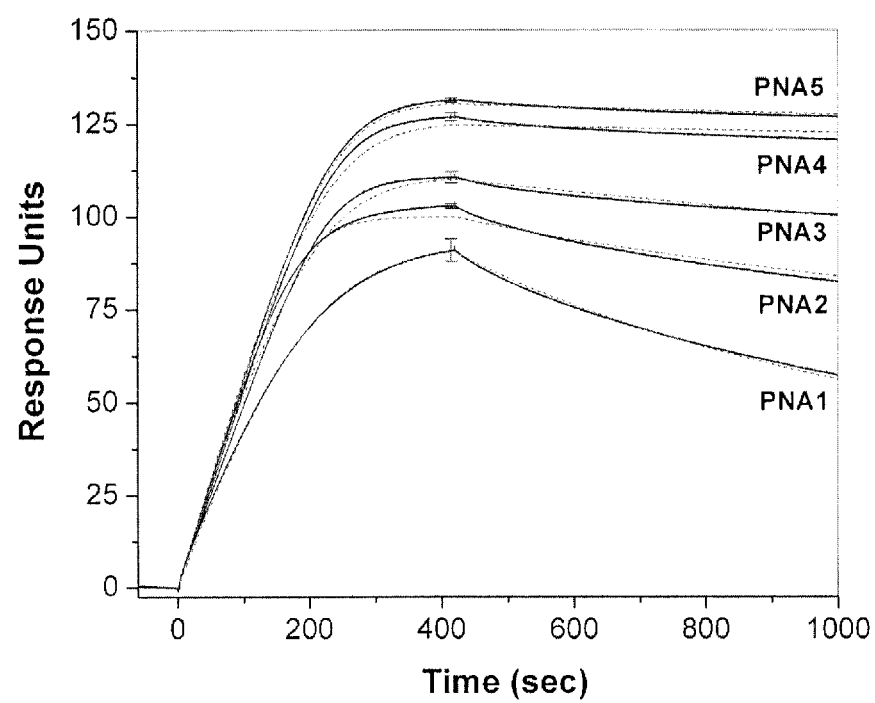
FIG. 4 illustrates surface plamon resonance (SPR) sensorgrams (solid black lines) and fits (dotted lines) for hybridization of PNA probes to immobilized complementary DNA. Solutions contained 30 nM PNA. Error bars at t=420 sec illustrate standard deviations for three separate trials.

While incorporation of additional miniPEG units does not further improve base-stacking, as is apparent from the similarities in the CD amplitudes, the presence of additional miniPEG's does help to tighten the helical pitch of the oligomers making them more rigid and compact. This is apparent from the temperature-dependent CD measurements, which showed a less dramatic reduction in the signal amplitude as a function of temperature change for the PNAS oligomer consisting of ten R-MP-γPNA groups as compared to the PNA2 oligomer having a single R-MP-γPNA group (FIG. 4). Even at a temperature as high as 80° C., a distinct CD profile is obtained for PNAS, indicating that base-stacking is occurring for this oligomer at a temperature of 80° C. In contrast, PNA2 is completely denatured at this temperature.

Figure 1B:
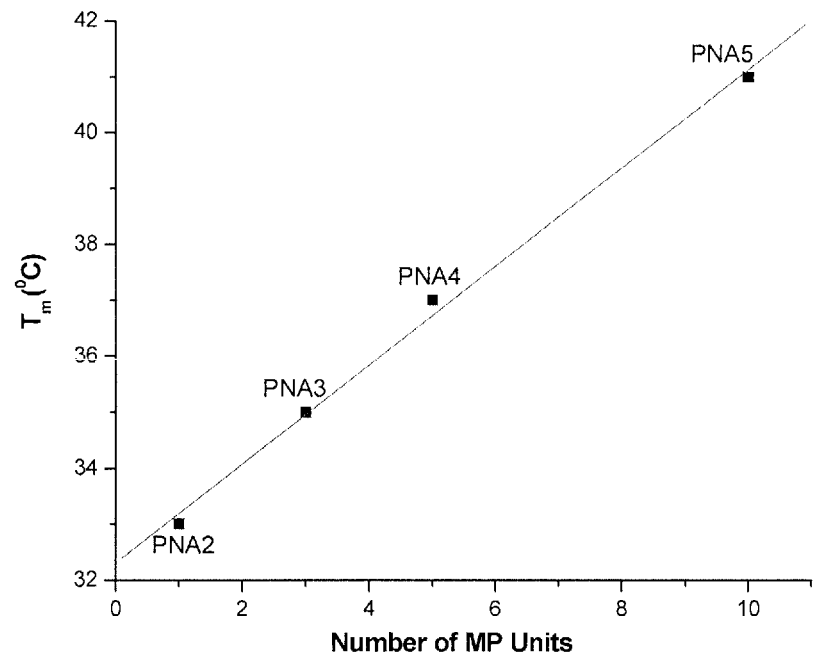
FIG. 1B is a graph correlating the stability of PNA oligomers to the number of inventive R-MP-γPNA monomers in the oligomer.
Figure 2A:
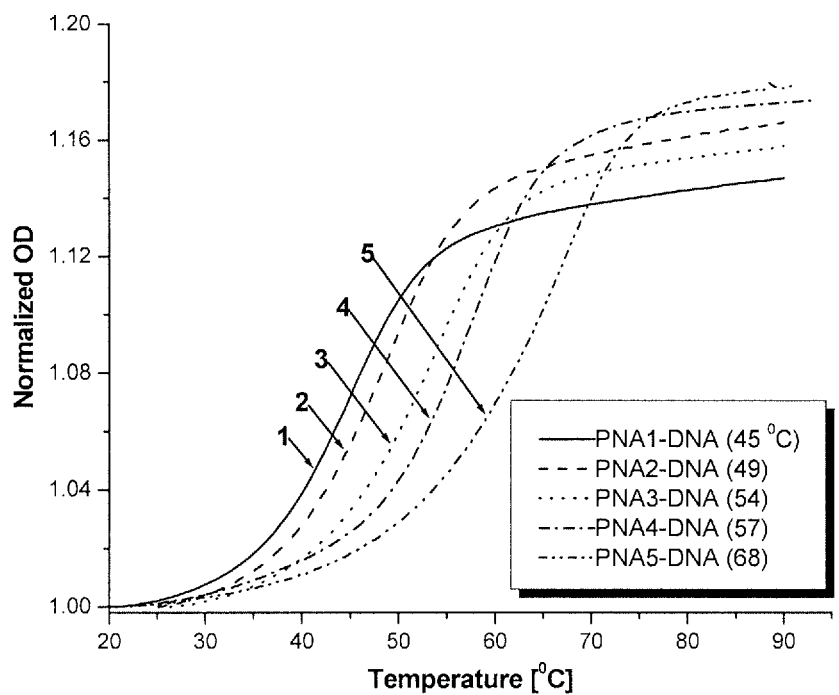
FIGS. 2A-2B illustrate UV-melting profiles of PNA-DNA (FIG. 2A) and PNA-RNA (FIG. 2B) hybrid duplexes at a strand concentration of 5 µM each in 10 mM sodium phosphate buffer at pH 7.4. While both the heating and cooling runs were performed because they both have nearly identical profiles UV-melting for only the heating runs are shown.
Figure 2B:
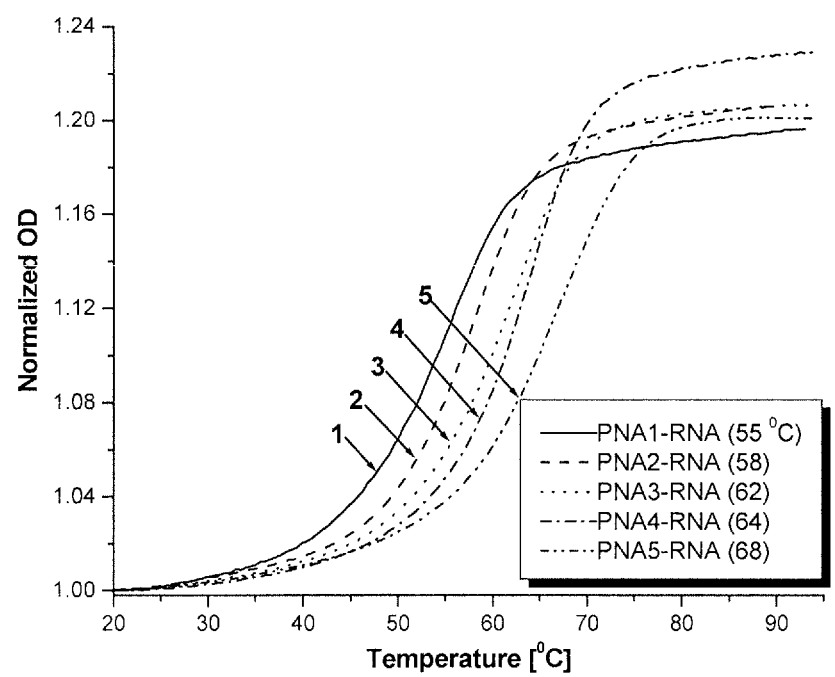

Thus, the overall stability of the oligomers increases linearly with the number of MP units incorporated (FIG. 1B). The fact that PNAS adopts a helical conformation most closely resembling that of a PNA-DNA or a PNA-RNA duplex suggests that it can hybridize to DNA and RNA more effectively than the other oligomers in this series.

change necessary to accommodate the $^{R\text{-}MP}$γPNA helix. The above hypothesis provides an explanation why an $^{S\text{-}Ala}$γPNA-DNA prefers a P-form helix, a helical structure that is intermediate between the A- and B-form DNA. It is also clear that the hybridization of a $^{R\text{-}MP}$γPNA to DNA and RNA requires the DNA and RNA moieties to conformationally alter to accommodate γPNA exigencies rather than the other way around.

Because the RNA strand is less accommodating to conformational changes, its hybridization to a fully modified $^{R\text{-}MP}$γPNA oligomer is less facile than hybridization of a DNA to the fully modified $^{R\text{-}MP}$γPNA oligomer.

Further insights related to the contribution of miniPEG to the stability of the PNA-DNA duplex was obtained from van't Hoff analysis. Data in Table 2 show the thermodynamic parameters associated with hybridization of PNA1 through 5 to a complementary DNA or RNA strand.

TABLE 2

Thermodynamic parameters for PNA-DNA and PNA-RNA duplexes

| | PNA-DNA† | | | | PNA-RNA‡ | | | |
|---|---|---|---|---|---|---|---|---|
| Oligo | $-\Delta H°$ (kJ/mol) | $-T\Delta S°$ (kJ/mol) | $-\Delta G°$ (kJ/mol) | $K_d$ | $-\Delta H°$ (kJ/mol) | $-T\Delta S°$ (kJ/mol) | $-\Delta G°$ (kJ/mol) | $K_d$ |
| PNA1 | 273 ± 5 | 224 ± 5 | 49 ± 1* | $2.5 \times 10^{-9}$ | 289 | 229 | 60 | $3.5 \times 10^{-11}$ |
| PNA2 | 319 ± 18 | 263 ± 16 | 54 ± 1 | $3.2 \times 10^{-10}$ | 333 | 232 | 68 | $1.2 \times 10^{-12}$ |
| PNA3 | 316 ± 11 | 256 ± 11 | 59 ± 1* | $5.1 \times 10^{-11}$ | 350 | 280 | 71 | $4.3 \times 10^{-13}$ |
| PNA4 | 329 ± 14 | 265 ± 12 | 65 ± 1 | $3.5 \times 10^{-12}$ | 356 | 283 | 73 | $1.7 \times 10^{-13}$ |
| PNA5 | 372 ± 11 | 294 ± 10 | 78 ± 2 | $4.6 \times 10^{-14}$ | 365 | 287 | 78 | $2.1 \times 10^{-14}$ |

†The averages of three trials (2 from concentration-dependence measurements + 1 from UV-melting curve fitting).
‡UV-melting curve fitting.
*Standard deviation is less than 1 kJ/mol. Temperature = 298 K.

2. Effect of MiniPEG on Thermal Stability of Oligomers

UV-melting experiments were performed to determine the effect of MP on the thermal stability of PNA oligomers following hybridization to DNA or an RNA. FIG. 3A illustrates that the incorporation of a single miniPEG side-chain stabilized a PNA-DNA duplex by 4° C. The extent of thermal stabilization gradually increased with additional minPEG units. However, increase in thermal stability tapers off to a value of about 2.3° C. per unit for the fully-modified oligomer, that is an oligomer made up of R-MP-γPNA groups only (e.g., PNA5).

A similar pattern is observed for a R-MP-γPNA-RNA duplex, but the observed increase in thermal stability is lower for a R-MP-γPNA-RNA duplex as compared to a R-MP-γPNA-DNA duplex (FIG. 3B). The enhancement in thermal stability of a R-MP-γPNA-RNA duplex is only 3° C. for the first R-MP-γPNA-monomer that is incorporated into the PNA oligomer and this gain in thermal stability reduces to about 1.2° C. per R-MP-γPNA monomer for an oligomer made entirely R-MP-γPNA (PNA5). In contrast the gain in thermal stability is about 2.3° C./unit for R-MP-γPNA-DNA duplexes.

It was further observed that while unmodified PNA1 binds more tightly to RNA than to DNA (differential $T_m$ ($\Delta T_m$) of 10° C.), the fully-modified miniPEG PNA5 displayed identical thermal stability with both RNA as well as with DNA. The apparent lack for preferential binding shown by PNA5 is not clearly understood but it may be due to rigidity of the PNA5 oligomer's backbone.

Without being bound to a particular theory, the present inventors believe that because PNA5 is more rigid and tightly wound when compared to PNA1 the rigid backbone limits conformational freedom necessary to accommodate the DNA and/or RNA template strands. Under such circumstances, the DNA and RNA strands taking part in hybridization themselves are forced to undergo a conformational The results show that the Gibbs binding free energy ($\Delta G°$) increases approximately linearly with increase in the number of miniPEG units for PNA-DNA duplexes, while increase in $\Delta G°$ is sigmoidal for PNA-RNA duplexes (FIGS. 3A and 3B).

The incorporation of a single miniPEG unit results in a net gain in binding free energy of about 5 kJ/mol for the PNA-DNA duplex and is less than 5 KJ/mol for a PNA-RNA duplex. The gain in binding free energy, moreover, is not linearly correlated to the number of $^{R\text{-}MP}$γPNA monomers in the PNA oligomer. Rather, most of the net gain in binding free energy is from the first two $^{R\text{-}MP}$γPNA monomers and decreases as more $^{R\text{-}MP}$γPNA monomers are introduced in the PNA oligomer of the PNA-RNA duplex. Additionally, a reduction in the equilibrium dissociation constant ($K_d$) by nearly five orders of magnitude was observed for a PNAS-DNA duplex while a decrease of about three orders of magnitude is observed for PNAS-RNA as compared to the PNA1-DNA and PNA1-RNA duplexes.

The binding free energy gain is believed to predominantly be from enthalpic contributions for both PNA-DNA and PNA-RNA duplexes as is shown by the gradual increase in the $\Delta H°$ term with the number of minPEG units present in the PNA. Further support that the gain in binding free energy is predominantly from enthalpic contributions stems from the observation that single-stranded PNA's adopt a compact globular form, presumably to minimize exposure of the hydrophobic core of nucleobases and the charge-neutral backbone to the aqueous solvent. It follows, therefore, that an enthalpic penalty would be incurred for unfolding the collapsed (globular) PNA in order to adopt the helical structure needed to participate in hybridization to a complementary DNA or RNA. Removal of this penalty by inducing a helical structure through the use of the miniPEG modified γ-PNA according to Formula I would translate to a more favorable enthalpic change during hybridization. See Table 2.

According to the present inventors, an additional enthalpic benefit of the modified backbone may be arise due to the formation of a network of structured water molecules that bridge the backbone amide protons to the adjacent nucleobases, stabilizing interactions that are more pertinent in a γPNA-DNA duplex than in a traditional PNA-DNA or PNA-PNA duplexes.

Surface plasmon resonance (SPR) analysis is used to study the hybridization kinetics of $^{R\text{-}MP}$γPNA-DNA and $^{R\text{-}MP}$γPNA-RNA duplexes. Briefly, SPR was performed as follows. According to one embodiment, the PNA probe was immobilized to the chip while the DNA target was captured from solution. In another embodiment, a biotinylated version of the DNA target is immobilized on a streptavidin-conjugated, carboxymethylated dextran chip at a relatively low surface density (ca. 100 response units) of DNA targets to limit mass transport effects on the association kinetics. Solutions containing 10-50 nM PNA oligomers are allowed to flow over the chip for about 420 seconds, at which point the flow is switched to a PNA-free buffer to allow net dissociation of the hybridized PNA.

Figure 6:
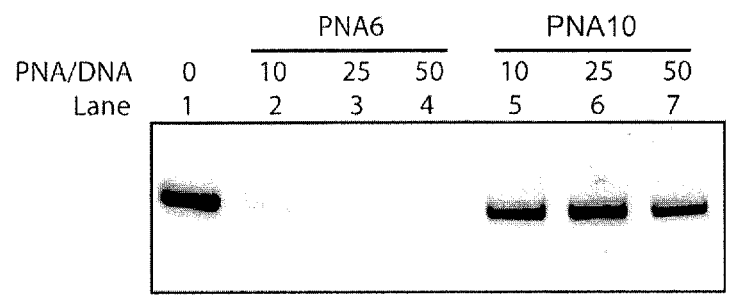
FIG. 6 illustrates the results of a non-denaturing gel-shift assay that was aimed at evaluating the extent of non-specific binding for an unmodified PNA oligomer (PNA6) and a oligomer containing the inventive R-MP-γPNA monomer (PNA10). A drastic reduction in the intensity of the DNA band was observed with increasing concentrations of PNA6.

Individual sensorgrams for the unmodified (PNA1) and $^{R\text{-}MP}$γ-modified (PNA2 through 5) oligomers at 30 nM concentration are shown in FIG. 6. While small variations are observed in the association kinetics, singly modified PNA2 appears to bind approximately twice as fast as the unmodified PNA. Fitting the data to a 1:1 binding model yields association rate constants ($k_a$) that range from $4.7 \times 10^5 M^{-1}s^{-1}$ to $9.7 \times 10^5 M^{-1}s^{-1}$ (Table 3).

TABLE 3

The association rate constant ($k_a$), dissociation rate constant ($k_d$), and equilibrium dissociation constant ($K_d$) for hybridization of PNA probes with a complementary DNA target.

| Oligomer | $k_a$ (M$^{-1}$s$^{-1}$) | $k_d$ (s$^{-1}$) | $K_d$ (M) |
| --- | --- | --- | --- |
| PNA1 | $4.7 \times 10^5$ | $13.0 \times 10^{-4}$ | $2.8 \times 10^{-9}$ |
| PNA2 | $9.7 \times 10^5$ | $4.1 \times 10^{-4}$ | $4.2 \times 10^{-10}$ |
| PNA3 | $6.2 \times 10^5$ | $1.9 \times 10^{-4}$ | $3.0 \times 10^{-10}$ |
| PNA4 | $6.6 \times 10^5$ | $0.3 \times 10^{-4\dagger}$ | $4.1 \times 10^{-11\dagger}$ |
| PNA5 | $8.0 \times 10^5$ | $0.4 \times 10^{-4\dagger}$ | $5.4 \times 10^{-11\dagger}$ |

†Indicates uncertainty due to the calculated value approaching the limits of detection of the instrument.

In contrast, significantly greater variability was seen in the dissociation phase of the experiment, with the dissociation rate constant ($k_d$) varying by at least a factor of 50. Equilibrium dissociation constants ($K_d$) calculated from the ratio of the dissociation and association rate constants are also given in Table 3. Unmodified PNA1 and fully-modified PNA5 have $K_d$=2.8 nM and 54 pM, respectively. The $K_d$ values for PNA1-3 determined by SPR (Table 3) are similar to those determined by UV melting experiments (Table 2). However, increasing divergences are observed for PNA4 and PNA5, with the SPR-derived values being 12- and 1200-fold greater, respectively than the $K_d$ values determined by UV melting experiments (Table 2).

This differences are attributed to the very small degrees of dissociation observed within the timescale of the SPR experiment. However these small differences in the degree of dissociation introduce a large uncertainty during the dissociation of the duplex and give rise to the differences in $K_d$ values.

In the above example, SPR results clearly demonstrate that enhanced affinity of the $^{R\text{-}MP}$γPNAs are due to the significantly slower dissociation kinetics of PNA oligomers containing one or more of the $^{R\text{-}MP}$γPNA monomers. Thus, the helical preorganization of the modified PNA may have a smaller contribution to faster hybridization kinetics than previously proposed. That is, hybridization is likely to require some structural reorganization of the complementary DNA strand, negating to some extent the benefit of pre-organizing the PNA oligomer to helical form.

CD, NMR, and X-ray data have shown that γPNAs derived from L-amino acids adopt a right-handed helix, and that the helix becomes more rigid as more γ-chiral units are added in the backbone. One would therefore expect a fully-modified PNA5 to hybridize to DNA and RNA targets with greater sequence selectivity than PNA1. To verify this hypothesis, thermal stabilities of PNA5-DNA and PNA5-RNA duplexes containing perfectly-matched (PM) and single-base mismatched (MM) targets were determined and compared to those from an earlier study with PNA1-DNA and PNA1-RNA duplexes. The results show that despite the strong binding affinity, PNA5 is able to discriminate between closely related sequences. The $\Delta T_m$ ranges from −17 to −21° C. for PNA5-DNA and -16 to −20° C. for PNA5-RNA containing a single-base mismatch (X=C, G, T), as compared to −10 to −14° C. for PNA1-DNA and −11 to −18° C. for PNA1-RNA duplex (Table 4). The level of sequence discrimination is greater for PNA5-DNA than for PNA1-DNA, and similar, if not slightly better, for PNA5-RNA as compared to PNA1-RNA. This result is consistent with PNA5 adopting a more rigid helical motif, which is less accommodating to structural mismatches as compared to PNA1.

TABLE 4

Sequence mismatch discrimination

PNA1: H-GCATGTTTGA-$^L$Lys-NH$_2$ (SEQ ID NO: 1)

PNA5: H-GCATGTTTGA-$^L$Lys-NH$_2$ (SEQ ID NO: 5)

DNA: 3'-CGTACAXACT-5, X = A, C, G, T (SEQ ID NO: 11)

RNA: 3'-CGUACAXACU-5, X = A, C, G, U (SEQ ID NO: 12)

| | $T_m$ (° C.) | | $T_m$ (° C.) | |
| --- | --- | --- | --- | --- |
| X-T | PNA1-DNA* | PNA5-DNA | PNA1-RNA* | PNA5-RNA |
| A-T | 45 | 68 | 55 | 68 |
| C<>T | 31 (−14)† | 47 (−21) | 37 (−18) | 48 (−20) |

TABLE 4-continued

Sequence mismatch discrimination

| | | | | | | | |
|---|---|---|---|---|---|---|---|
| G<>T | 31 | (-14) | 48 | (-20) | 44 | (-11) | 52 (-16) |
| T(U)<>T | 35 | (-10) | 51 | (-17) | 40 | (-15) | 48 (-20) |

*The data for PNA1-DNA and PNA1-RNA mismatched binding was taken from Dragulescu-Andrasi, A.; et al., J. Am. Chem. Soc. 2006, 128, 10258-10267. ¹The value in the parenthesis indicates ΔTm between the perfect match and mismatch.

Effect of MiniPEG on Aqueous Solubility and Aggregation

To determine whether inclusion of miniPEG in the backbone of a Formula I PNA has an effect on water solubility of the resultant oligomer, saturating concentrations of PNA6 through 10 (Table 1) were prepared in water and the concentrations of each solution was measured by UV-spectroscopy. The incorporation of a single MP unit enhances the solubility of PNA6 by nearly 2-fold (Table 5). The solubility of the oligomers is further improved, albeit to a smaller extent, with additional MP units.

TABLE 5

Saturated concentrations of PNA oligomers

| Oligomer | # MP units | Sat. conc. (mM) |
|---|---|---|
| PNA6 | 0 | 39 |
| PNA7 | 1 | 76 |
| PNA8 | 3 | 108 |
| PNA9 | 5 | 350 |
| PNA10 | 8 | >500 |

FRET was used to study whether incorporation of a miniPEG unit in the backbone of PNA can help reduce aggregation. Different concentrations of unmodified PNA1X/PNA1Y and homologous γ-modified PNA4X/PNA4Y pairs (Table 1) are prepared by mixing equimolar ratios of the individual oligomers in sodium phosphate buffer. The samples were excited at 475 nm, the $\lambda_{max}$ of FITC, and emission was recorded from 480 to 700 nm. Upon aggregation, in which the oligomers bearing FITC and TAMRA come into contact with one another, excitation at 475 nm leads to energy transfer from FITC to TAMRA because of the proximity of the two chromophores. Comparison of the FRET efficiencies of the two systems at different concentrations, therefore, can provide an assessment of the effect of miniPEG on intermolecular interaction of PNA's.

Figure 5A:
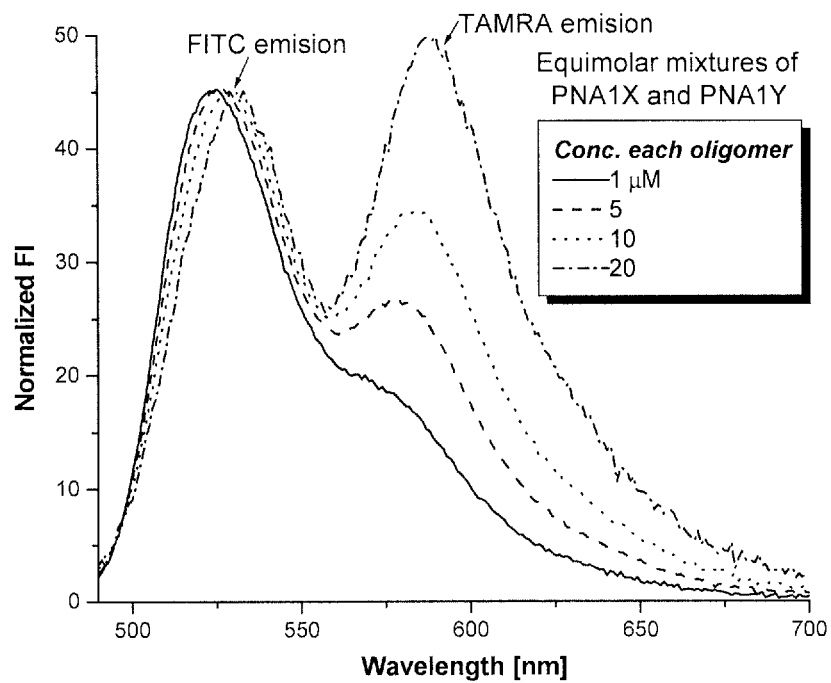
FIGS. 5A-5B show fluorescent spectra of PNA1X/PNA1Y (FIG. 5A) and PNA4X/PNA4Y (FIG. 5B) pairs at different concentrations. The samples were prepared by mixing equimolar ratios of the oligomers in 10 mM sodium phosphate buffer at pH 7.4. Samples were excited at 475 nm (FITC $\lambda_{max}$) and the emissions were recorded from 480 to 700 nm. The spectra were normalized with respect to the FITC emission.
Figure 5B:
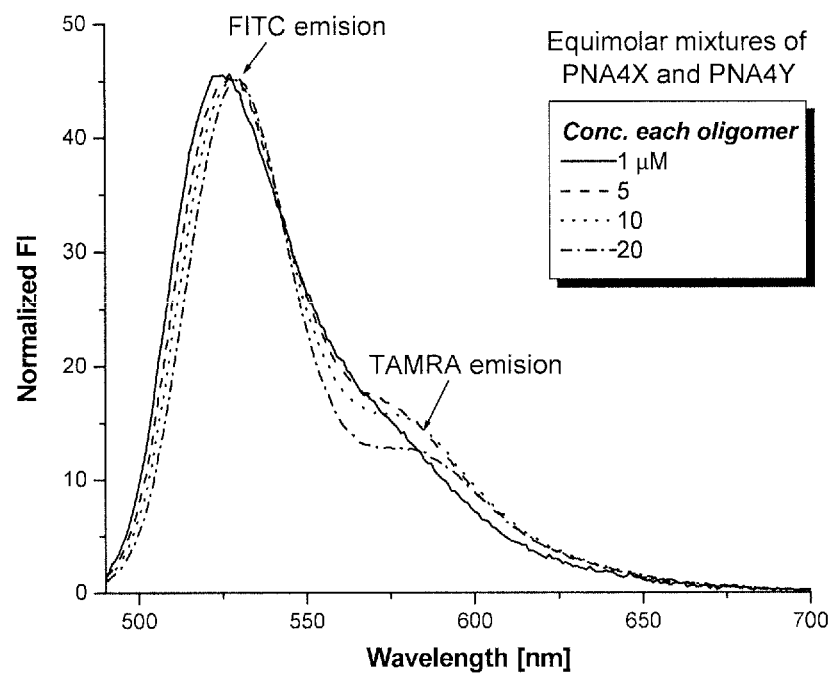

As illustrated by FIG. 5A, when the concentration for each unmodified PNA oligomer is as low as 1 µM, a small but noticeable emission appeared at 580 nm, indicating some aggregation between PNA1X and PNA1Y. The extent of aggregation is further intensified with increasing concentrations of oligomers, apparent from the fluorescent intensity of TAMRA at ~580 nm upon excitation of the FITC donor at 475 nm.

In contrast, at a concentration of 20 µM, the point at which nearly 70% FRET efficiency is observed for unmodified PNA1X/PNA1Y pair, about 5% FRET efficiency is observed for the γ-modified PNA4X/PNA4Y pair. These results indicate that the γ-modified PNA pair does not interact with each other as much as the unmodified PNAs. The distinction is also apparent from photographs of the samples illuminated using a short-wavelength (254 nm), hand-held UV-lamp. The PNA1X/PNA1Y solution displayed a light orange emission at room temperature and yellow-green hue at 90° C., an indication of the aggregate dissociating upon heating. In contrast, the PNA4X/PNA4Y solution displayed the same color, yellow-green, at room temperature as well as at 90° C., indicating that the oligomers are well dispersed even at room temperature. Thus, the R-MP-γ-modification imparts not only enhanced solubility to PNA, but also suppresses aggregation.

It has been documented that at moderate concentrations, PNA tends to aggregate and stick to surfaces and other macromolecules in a nonspecific manner. Such interactions can lead to off-target binding and cytotoxic effects, when employed in the cellular context. Among the macromolecules that PNA is known to interact nonspecifically with are nucleic acids and proteins.

To assess the extent of off-target binding of PNA and $^{R\text{-}MP}\gamma$PNA, a gel-shift assay is performed. In this case, a DNA fragment, 171 bp in length, is incubated with different concentrations of PNA6 and PNA10 (Table 1) in 10 mM sodium phosphate buffer at 37° C. for 16 hr. The two oligomers contain identical nucleobase sequence but differ from another at the γ-backbone. PNA6 is unmodified, whereas PNA10 is modified at every other position with R-MP-γ side-chain. Following incubation, the samples are separated on non-denaturing polyacrylamide gel and stained with SYBR-Gold.

Since the target does not contain a complementary sequence to the oligomers, no binding is expected to take place, in which case the intensity of the DNA band should remain fairly constant, independent of the PNA6 and PNA10 concentrations. Instead, a drastic reduction in the intensity of the DNA band is observed with increasing concentrations of PNA6 (FIG. 6). At 10 µM (corresponding to a PNA/DNA ratio of 25:1) or higher, the DNA band completely disappeared from the gel.

In contrast, for γ-modified PNA10 the intensity of the DNA bands remained fairly constant even at a concentration as high as 20 µM (PNA/DNA ratio of 50:1). This result is consistent with the solubility and FRET data, indicating that incorporation of miniPEG at the γ-backbone not only improves the hybridization properties and water solubility of PNA but also helps to reduce nonspecific binding with other macromolecules as well.

Gamma-backbone modified PNA's according to Formula I as well as oligomers containing the Formula I PNA's are provided, in accordance with the invention, to improve design and utility of PNA-based therapeutic and diagnostics. For instance, improvements in hybridization properties can enable R-MPγPNAs to invade double helical DNA and structured RNA that may not be permissible with other oligonucleotide mimics. Enhancements in water solubility will facilitate the handling and processing of PNA while lessening the concerns for nonspecific binding and cytotoxic effects. Improvements in these areas, along with the flexibility of synthesis whereby other chemical functionalities can be installed at the γ-backbone with ease, will expand the utility of PNA into other scientific disciplines, including drug discovery and nanotechnology.

What is claimed is:

1. A peptide nucleic acid (PNA) monomer having the following formula:

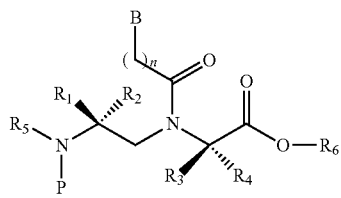

wherein

B is adenine, guanine, cytosine, thymine, or uracil;

P is selected from the group consisting of hydrogen (H), 9-fluorenylmethyloxycarbonyl (Fmoc), t-butyloxycarbonyl (Boc), benzyloxycarbonyl (Cbz), benzyl (Bn), tosylate (Tos), allyloxycarbonyl (alloc), benzhydryloxycarbonyl (Bhoc), trityl (Trt), monomethoxytrityl (MMT) and dimethoxytrityl (DMT);

each of $R_1$ and $R_2$ is independently selected from the group consisting of hydrogen (H), linear or branched ($C_1$-$C_8$)alkyl, ($C_2$-$C_8$)alkenyl, ($C_2$-$C_8$)alkynyl, ($C_1$-$C_8$)hydroxylalkyl, ($C_3$-$C_8$)aryl, ($C_3$-$C_8$)cycloalkyl, ($C_3$-$C_8$)aryl($C_1$-$C_6$)alkylene, ($C_3$-$C_8$)cycloalkyl($C_1$-$C_6$)alkylene, and

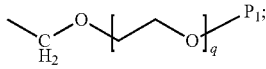

provided that at least one of $R_1$ and $R_2$ is

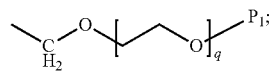

each of $R_3$ and $R_4$ is independently selected from the group consisting of hydrogen (H) and

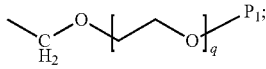

$R_5$ is selected from the group consisting of hydrogen (H), linear or branched ($C_1$-$C_8$)alkyl, ($C_2$-$C_8$)alkenyl, ($C_2$-$C_8$)alkynyl, ($C_1$-$C_8$)hydroxylalkyl, ($C_3$-$C_8$)aryl, ($C_3$-$C_8$)cycloalkyl, ($C_3$-$C_8$)aryl($C_1$-$C_6$)alkylene and ($C_3$-$C_8$)cycloalkyl($C_1$-$C_6$)alkylene;

$R_6$ is selected from the group consisting of hydrogen (H), linear or branched ($C_1$-$C_8$)alkyl, substituted or unsubstituted ($C_3$-$C_8$)aryl and ($C_3$-$C_8$)aryl($C_1$-$C_6$)alkylene;

P₁ is selected from the group consisting of hydrogen (H), linear or branched (C₁-C₈)alkyl, 9-fluorenylmethyloxycarbonyl (Fmoc), t-butyloxycarbonyl (Boc), benzyloxycarbonyl (Cbz), benzyl (Bn), tosylate (Tos), allyloxycarbonyl (alloc), trityl (Trt), monomethoxytrityl (MMT) and dimethoxytrityl (DMT);

n is an integer from 0 to 10, inclusive; and q is an integer from 1 to 10, inclusive.

2. The PNA monomer of claim 1, wherein one of R₁ and R₂ is independently

[structure]

and the other of R₁ and R₂ is independently hydrogen (H).

3. The PNA monomer of claim 2, wherein R₁ is

[structure]

and R₂ is hydrogen (H).

4. The PNA monomer of claim 2, wherein R₂ is

[structure]

and R₁ is hydrogen (H).

5. The PNA monomer of claim 1, wherein

R₁ is —CH₂(OCH₂CH₂)$_q$OH; —CH₂(OCH₂CH₂)$_q$OCH₃; —CH₂(OCH₂CH₂)$_q$OCH₂CH₃; or —CH₂(OCH₂CH₂)$_q$OC(CH₃)₃;

R₂ is H;

R₃, R₄, R₅, and R₆ each independently are H;

P is selected from the group consisting of H, 9-fluorenylmethyloxy carbonyl (Fmoc), tert-butyloxycarbonyl (Boc), benzyloxycarbonyl (Cbz), tosylate (Ts), benzyl (Bn), allyloxycarbonyl (alloc), trityl (Trt), dimethoxytrityl (DMT), and monomethoxytrityl (MMT);

n is 0, 1, or 2; and q is 1, 2, 3, 4, or 5.

6. The PNA monomer of claim 5, wherein P is H; n is 1; and q is 1, 2, or 3.

7. The PNA monomer of claim 1, wherein R₃ and R₄ are H; R₅ is H or —CH₃; R₆ is H or —CH₃; n is 1; and q is 1, 2 or 3.

8. The PNA monomer of claim 7, wherein P is 9-fluorenylmethyloxy carbonyl (Fmoc) or tert-butyloxycarbonyl (Boc).

9. The PNA monomer of claim 1, selected from the following compounds:

[structures of four compounds with thymine, cytosine, adenine, and guanine nucleobases]

wherein P₁ is hydrogen (H), tert-butyloxycarbonyl (Boc) or 9-fluorenylmethyloxy carbonyl (Fmoc); and R is —(OCH₂CH₂)$_q$OH; —(OCH₂CH₂)$_q$OCH₃; —(OCH₂CH₂)$_q$OCH₂CH₃; or —(OCH₂CH₂)$_q$OC(CH₃)₃.

10. The PNA monomer of claim 1 having the following formula:

[structure]

wherein y is 1, 2, 3, or 4 (inclusive).

11. A PNA oligomer comprising the PNA monomer of claim 1.

12. The PNA oligomer of claim 11, wherein one of R₁ and R₂ is independently

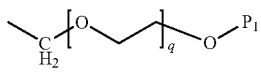

and the other of $R_1$ and $R_2$ is independently hydrogen (H).

13. The PNA oligomer of claim 12, wherein $R_1$ is

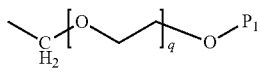

and $R_2$ is hydrogen (H).

14. The PNA oligomer of claim 12, wherein $R_2$ is

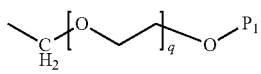

and $R_1$ is hydrogen (H).

15. The PNA oligomer of claim 11, wherein $R_1$ is —$CH_2(OCH_2CH_2)_qOH$; —$CH_2(OCH_2CH_2)_qOCH_3$; —$CH_2(OCH_2CH_2)_qOCH_2CH_3$; or —$CH_2(OCH_2CH_2)_qOC(CH_3)_3$;

$R_2$ is H;

$R_3$, $R_4$, $R_5$, and $R_6$ each independently are H;

P is selected from the group consisting of H, 9-fluorenylmethyloxy carbonyl (Fmoc), tert-butyloxycarbonyl (Boc), benzyloxycarbonyl (Cbz), tosylate (Ts), benzyl (Bn), allyloxycarbonyl (alloc), trityl (Trt), dimethoxytrityl (DMT), and monomethoxytrityl (MMT);

n is 0, 1, or 2; and q is 1, 2, 3, 4, or 5.

16. The PNA oligomer of claim 11, wherein P is H; n is 1; and q is 1, 2, or 3.

17. The PNA oligomer of claim 11, wherein $R_3$ and $R_4$ are H; $R_5$ is H or —$CH_3$; $R_6$ is H or —$CH_3$; n is 1; and q is 1, 2 or 3.

18. The PNA oligomer of claim 17, wherein P is 9-fluorenylmethyloxy carbonyl (Fmoc) or tert-butyloxycarbonyl (Boc).

19. The PNA oligomer of claim 11, comprising a PNA monomer selected from the following compounds:

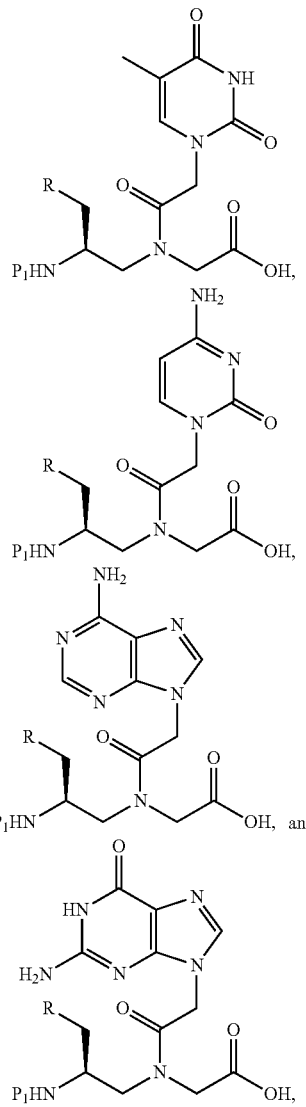

wherein $P_1$ is hydrogen (H), tert-butyloxycarbonyl (Boc) or 9-fluorenylmethyloxy carbonyl (Fmoc); and R is —$(OCH_2CH_2)_qOH$; —$(OCH_2CH_2)_qOCH_3$; —$(OCH_2CH_2)_qOCH_2CH_3$; or —$(OCH_2CH_2)_qOC(CH_3)_3$.

* * * * *

UNITED STATES PATENT AND TRADEMARK OFFICE
CERTIFICATE OF CORRECTION

PATENT NO. : 10,793,605 B2  
APPLICATION NO. : 16/362579  
DATED : October 6, 2020  
INVENTOR(S) : Danith H. Ly et al.

Page 1 of 1

It is certified that error appears in the above-identified patent and that said Letters Patent is hereby corrected as shown below:

In the Specification

Column 1, Line 25, please delete "Service" and insert -- Science --.

In the Claims

Claim 10, at Column 32, Line 55, please delete " 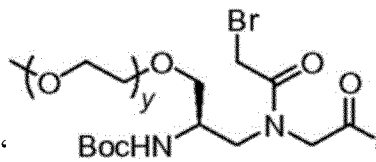 ," and insert

-- 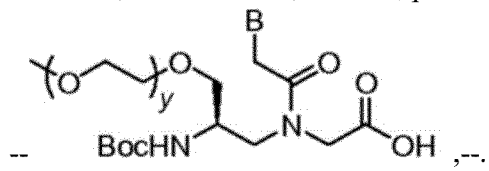 ,--.

Signed and Sealed this  
Seventh Day of December, 2021

Drew Hirshfeld  
*Performing the Functions and Duties of the*  
*Under Secretary of Commerce for Intellectual Property and*  
*Director of the United States Patent and Trademark Office*